US012527680B1

(12) United States Patent
McGrath

(10) Patent No.: US 12,527,680 B1
(45) Date of Patent: Jan. 20, 2026

(54) ARM SUPPORT APPARATUS

(71) Applicant: Steven McGrath, Napa, CA (US)

(72) Inventor: Steven McGrath, Napa, CA (US)

(73) Assignee: Renuvia Pro, LLC, Napa, CA (US)

(*) Notice: Subject to any disclaimer, the term of this patent is extended or adjusted under 35 U.S.C. 154(b) by 0 days.

(21) Appl. No.: 19/097,549

(22) Filed: Apr. 1, 2025

Related U.S. Application Data

(63) Continuation-in-part of application No. PCT/US2022/051024, filed on Nov. 27, 2022, and a continuation-in-part of application No. 18/970,874, filed on Dec. 5, 2024, now Pat. No. 12,290,464, which is a continuation-in-part of application No. 18/511,072, filed on Nov. 16, 2023, now abandoned, said application No. PCT/US2022/051024 is a continuation-in-part of application No. 17/830,081, filed on Jun. 1, 2022, now Pat. No. 11,547,592.

(60) Provisional application No. 63/294,588, filed on Dec. 29, 2021.

(51) Int. Cl.
*A61F 5/37* (2006.01)
*A61F 5/058* (2006.01)

(52) U.S. Cl.
CPC .......... *A61F 5/3723* (2013.01); *A61F 5/3753* (2013.01); *A61F 5/05858* (2013.01)

(58) Field of Classification Search
CPC ........ A61F 5/0118; A61F 5/37; A61F 5/3715; A61F 5/3723; A61F 5/373; A61F 5/3738; A61F 5/3753; A61G 7/075; A61G 13/1235
See application file for complete search history.

(56) References Cited

U.S. PATENT DOCUMENTS

| | | | | | |
|---|---|---|---|---|---|
| 5,224,637 | A * | 7/1993 | Colombo | A47D 13/029 | 224/159 |
| 8,109,273 | B2 * | 2/2012 | Golden | A61F 5/32 | 602/5 |
| 8,454,544 | B2 * | 6/2013 | Barnes | A61F 5/3753 | 602/19 |
| 9,700,152 | B2 * | 7/2017 | Telford | A47D 13/025 | |
| 10,736,767 | B2 * | 8/2020 | Boileau | A61F 5/3753 | |
| 12,115,094 | B1 * | 10/2024 | Chunchanakatte Melukote | A61F 5/3723 | |
| 12,290,464 | B1 * | 5/2025 | McGrath | A61F 5/05858 | |
| 2010/0152635 | A1 * | 6/2010 | Borden | A61F 5/3738 | 602/4 |
| 2013/0317401 | A1 * | 11/2013 | Joslin | A61F 5/3738 | 602/4 |

(Continued)

Primary Examiner — Keri J Nelson
(74) *Attorney, Agent, or Firm* — Staniford Tomita LLP

(57) ABSTRACT

The arm brace supports an injured arm during rehabilitation. The arm brace has a wrap member, an arm support member, and an arm sleeve member. The wrap member is secured around a hip and a thigh of a user. The arm support member is secured to a side of the wrap member with couplings including V straps. This configuration provides a platform structure that supports the arm sleeve that partially surrounds and protects the forearm. The arm brace does not require a shoulder strap, a neck strap for support and any other upper body supports. The brace provides a stable support structure that immobilizes the arm regardless of the position of the patient. The hand extends out from a front end of the brace so the user can perform activities such as eating, typing, and grasping.

18 Claims, 35 Drawing Sheets

(56) References Cited

U.S. PATENT DOCUMENTS

| | | | | |
|---|---|---|---|---|
| 2015/0080776 | A1* | 3/2015 | Davis | A61F 5/3738<br>602/4 |
| 2016/0022468 | A1* | 1/2016 | Lo | A61F 5/05858<br>602/20 |
| 2023/0338183 | A1* | 10/2023 | Cushing | A61F 5/3753 |

* cited by examiner

ARM SUPPORT APPARATUS

CROSS-REFERENCE TO RELATED APPLICATIONS

This application is a continuation in part of U.S. patent application Ser. No. 18/970,874, "Arm Support Apparatus" filed Dec. 5, 2024, which is a continuation in part of Ser. No. 18/511,072, "Arm Support Apparatus" filed Nov. 16, 2023, which is a continuation in part of PCT Patent Application No. PCT/US22/51024, titled "Arm Support Apparatus" filed Nov. 27, 2022, which is a continuation in part of U.S. patent application Ser. No. 17/830,081, "Arm Support Apparatus" filed Jun. 1, 2022, now U.S. Pat. No. 11,547,592 which claims priority to U.S. Provisional Patent Application No. 63/294,588, titled "Load-bearing shoulder immobilizer and arm support, without the need for a shoulder strap." PCT Patent Application No. PCT/US22/51024 and U.S. patent application Ser. Nos. 18/970,874, 18/511,072, 17/830,081, and 63/294,588 are hereby incorporated by reference in their entirety.

FIELD OF THE INVENTION

The present invention is directed towards a brace for arm and/or shoulder immobilization.

BACKGROUND

When people injure their arms and/or shoulders, it can be necessary to immobilize the arm to protect the limb and supports the weight of the arm to allow the arm and/or shoulder to heal. Similarly, when people have arm or shoulder surgery, it can be necessary to immobilize the arm to allow the arm and/or shoulder to recover from the surgery. The most common immobilization devices are arm braces and slings. However, there are many drawbacks with existing arm braces and slings.

Many prior art braces and slings require a strap that wraps around the neck or opposing shoulder which can be uncomfortable. Shoulder slings as well as the majority of shoulder immobilizers utilize a strap around the neck or opposite shoulder to suspend the weight of the arm. The average arm weighs about ten pounds. Thus, when prior art braces and slings are used, a force of about ten pounds can be applied to the neck or opposite shoulder. This method of suspending the weight can create neck and shoulder pain, fatigue, and discomfort in a short period of time.

Prior art braces and slings hold the weight of the arm and forearm in suspension but fail to fully support the arm and shoulder. The hand position is generally held against the torso, so the hand of the supported arm is not in a functional position. The prior art sling can be used with an abduction pillow to support an arm. However, this two piece configuration has drawbacks. Typically, slings are assembled and fitted to the patient by the surgical team and placed on the patient's arm while they are asleep. Many patients find it difficult to get their arms into and out of the sling. This may be because the sling is made of a loose fabric that may tend to cling to and move with the patient's arm rather than a more rigid structure that is more easily separated from the arm.

In addition, prior art shoulder immobilizers provide little or no rotational stability, meaning that these devices do not stabilize the arm when the patient's body rotates out of a vertical torso orientation. Shoulder immobilizers can be functional while the patient is standing or sitting upright. However, the immobilizers can create issues of discomfort or even risk further injury when the users reposition or lie on their side in lateral decubitus. Sleeping can be very difficult after surgery or any injury of the shoulder and therefore rotational stability is very important for comfort which is necessary for proper rest and sleep while the patient is in a horizontal position. Similarly, prior art shoulder immobilizers can be very uncomfortable when the patient exercises or jogs because the arm support bounces with any vertical movement. Thus, prior art shoulder immobilizers and slings can only support the weight of an arm in limited conditions and these devices fail to provide a functional, comfortable, and load-bearing support and protection of the arm when the patient is not standing or sitting upright.

What is needed is an improved arm brace that is more comfortable because it does not require a strap that wraps around the neck or shoulder and fully supports the weight of the arm with rotational stability, and allows the hand to be supported in a functional position.

SUMMARY OF THE INVENTION

The inventive arm brace is a substantial improvement over the prior art which requires that the entire weight of the arm be supported by a shoulder or a neck and can provide superior protection and support for the forearm in a functional and comfortable position. The arm brace includes a soft elastic arm pad mounted on a support plate that is attached to a support structure that is secured to a side of the patient with a waist strap and leg straps. The patient's forearm can be placed on an arm pad that can be a contoured elastic foam cushion. In some embodiments, the arm pad can have a deep cut out slot that can modified or custom fitted to fit the patient's forearm. The arm pad can surround, support, and protect the forearm. The slot in the arm pad can be open on the top, supported on the side surfaces and elbow end and have an open hand end that allows the patient's hand to extend out of the arm brace so that the hand can be used for various manual tasks.

The inventive brace functions as a load-bearing column that supports the arm platform and the weight of the forearm. The structural brace mechanism can also include an upper support structure coupled to an upper portion of a hip hinge and a lower support structure coupled to a lower portion of the hip hinge. The brace mechanism can be coupled to the side of the patient and positioned with the hip hinge adjacent to the patient's hip. The upper support structure can be secured to the waist of the patient with a waist strap and the lower support structure can be secured to the thigh by one or more leg straps. The hip hinge allows the inventive brace to provide arm support while simultaneously allowing the leg to rotate about the hip joint while the patient is standing, sitting, walking, running, or performing various other bodily movements.

Thus, in contrast to the prior art slings that support the weight of the arm with a tension mechanism suspension from the neck or shoulder, the inventive arm brace supports the forearm with a load-bearing/supporting compression structural column. The arm can rest in a contoured foam cushion, sitting upon an arm platform which is supported by a movable brace structure that is connected to the upper leg and waist with straps. The contoured foam cushion arm pad, which holds the user's forearm, can be releasably coupled to the arm platform with a hook and loop mechanism. The hook or loop materials can be adhesively attached to the bottom surface of the cushion arm pad and the top surface of the arm platform. For example, a hook material can be attached to the bottom surface of the cushion and a loop material can be attached to the top surface of the arm platform or the loop material can be attached to the bottom surface of the cushion and a hook material can be attached to the top surface of the arm platform. The arm pad can be positioned at the desired orientation on the arm platform and these components can be pressed together to secure the arm pad in place.

The arm platform, which supports the weight of the user's arm and cushion, can be connected by fasteners such as nuts and bolts or other secure fastening means to the upper support structure of the brace bracket or other extension from the upper part of the brace. Thus, the arm pad and platform can be adjusted to provide a comfortable arm position that can also allow the hand to perform limited functional activities such as typing, drawing, writing, grasping, etc.

The inventive arm brace is also highly adjustable so that it can be properly fitted and used by a wide variety of patient sizes. The brace can be constructed with several elongated members that are adjustable in length and can be secured in the desired lengths. For example, a horizontal portion of the upper support structure can control the horizontal position of the arm support and arm pad. The horizontal member can be shortened to move the arm pad to be very close to the patient's torso or extended to move the arm pad away from the torso. The rotational angle of the arm pad can also be adjusted. For example, the arm pad can be placed directly against the torso to position the forearm across the torso which can support and protect the forearm.

If the patient needs to use the supported hand, the arm support and arm pad can be rotated so that the hand is positioned away from the torso so that the hand can be used to perform tasks such as typing, writing, drawing, object grasping, etc. In an embodiment, a rotational mechanism such as a swivel can be mounted between the upper support structure and the arm support. For example, the rotational mechanism or swivel can be a screw that is in a vertical orientation. The arm support can be rotated into the desired position and then the screw can be tightened to secure the arm support to the upper portion of the upper support structure.

The arm brace can also be adjusted to fit different sized users. The lower vertical portion of the upper support structure that extends between the hinge and the arm platform can be adjusted in length to properly fit the patient's hip to forearm distance. For example, a vertical length of the upper support structure can be extended for taller patients and shortened for shorter patients. Similarly, the length of the lower support structure below the hinge can be adjusted in length. The vertical length of the lower support structure can be extended for taller patients and shortened for shorter patients. The brace structure can be secured to the patient with a waist strap and leg straps, that fit a wide variety of body sizes. These straps can be tightened to provide support for the brace structure.

As discussed, the brace includes a hinge that has an axis of rotation. The brace can be adjusted so that the axis of rotation is aligned with the axis of rotation of the lateral hip. The hinge can allow full hip flexion while the patient is wearing the arm brace. The hinge can also have a locking mechanism that can restrict or prevent the rotation of the hinge and brace. For example, the lock can allow the brace hinge to rotate within a limited range of angles or lock the brace at any angle of flexion or in full extension. By locking the hinge of the brace, the stability of the arm brace can be improved.

In other embodiments, the brace structure can be used for other applications. For example, the arm support can be replaced with a desk that can be used to support other manual devices such a computer or a stand for other tools such as soldering stations, pipe tools, etc.

DETAILED DESCRIPTION

Figure 1:
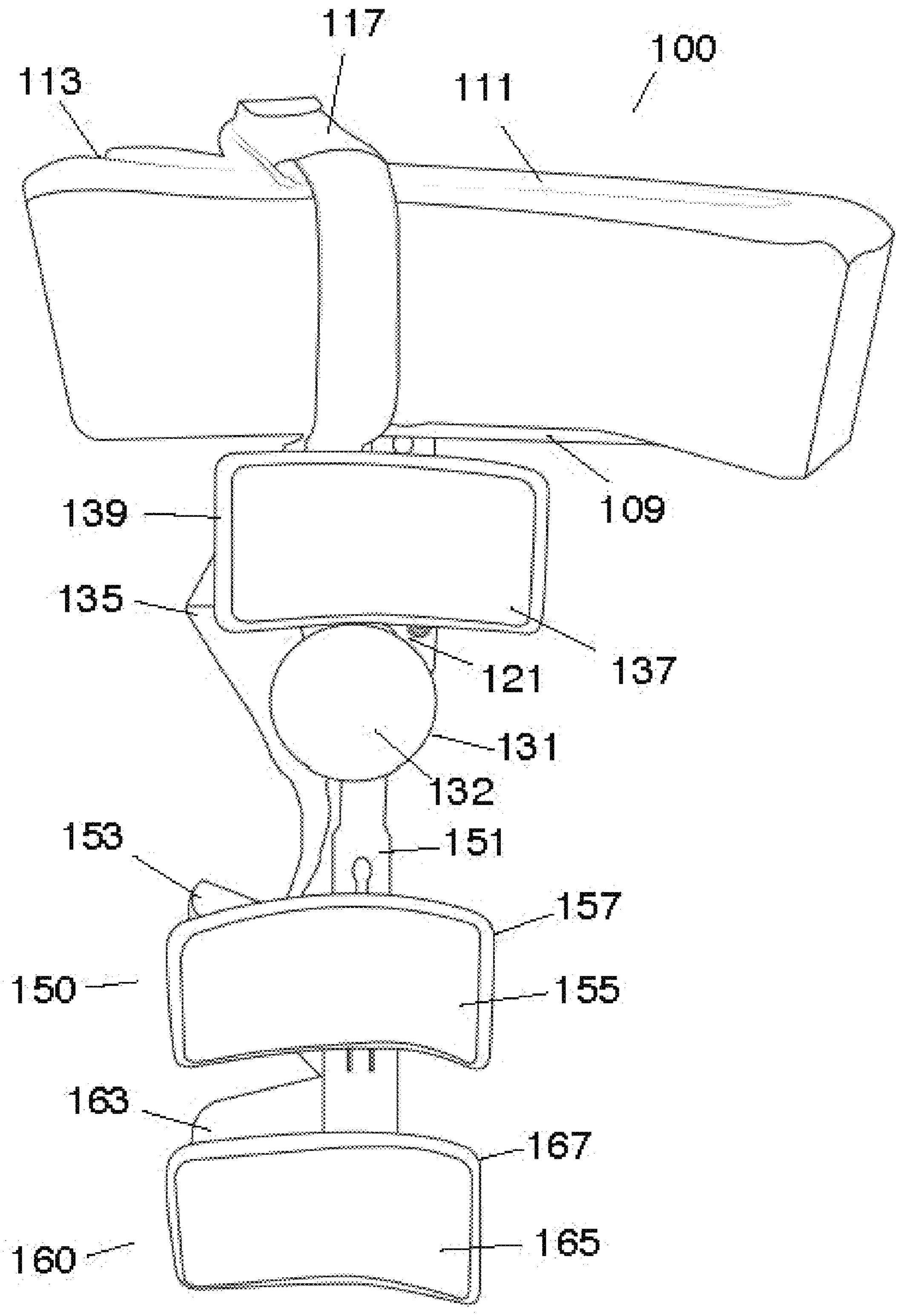
FIG. 1 illustrates a left side view of an embodiment of a right arm support with the hinge straight.
Figure 2:
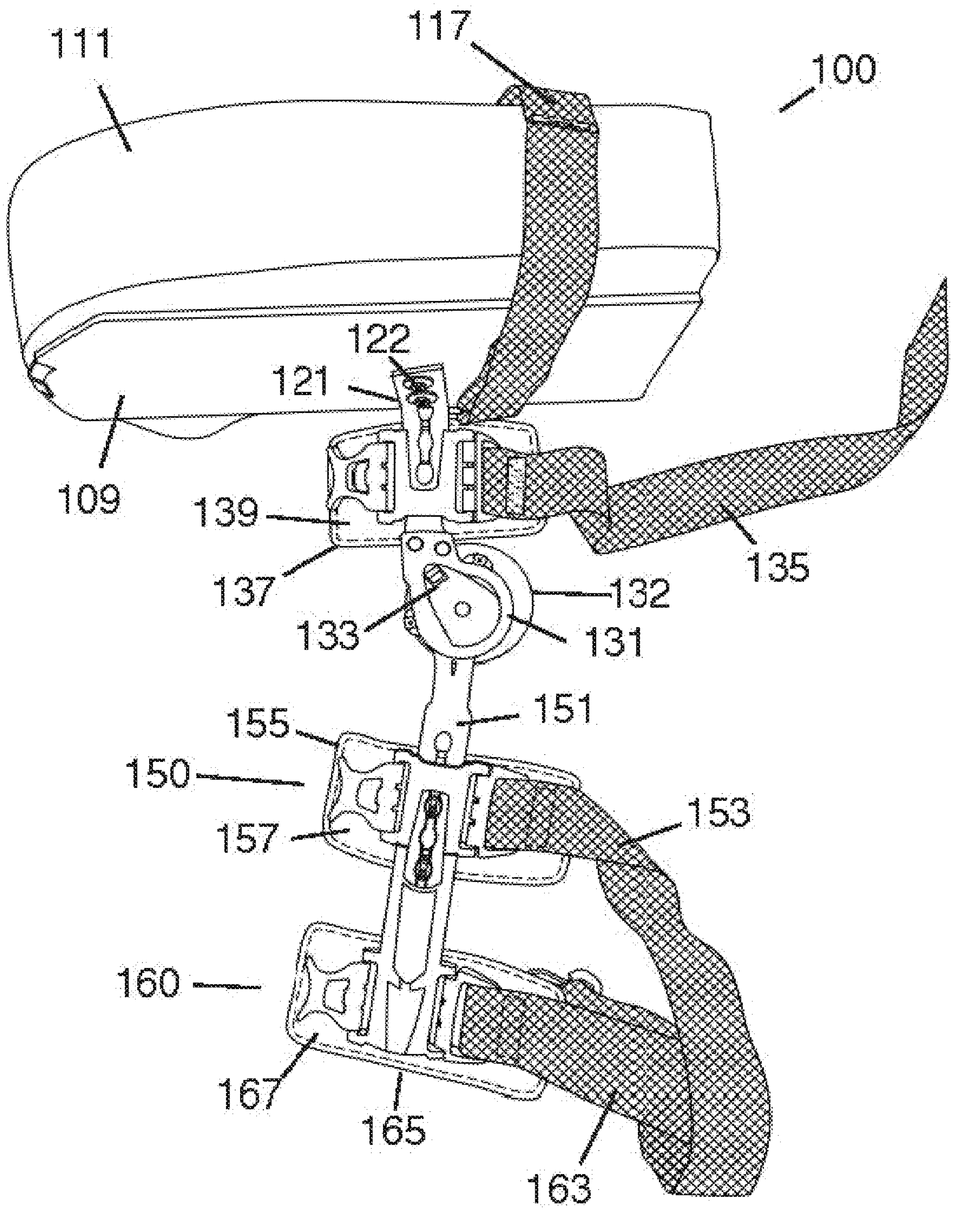
FIG. 2 illustrates a right side view of an embodiment of a right arm support with the hinge straight.
Figure 3:
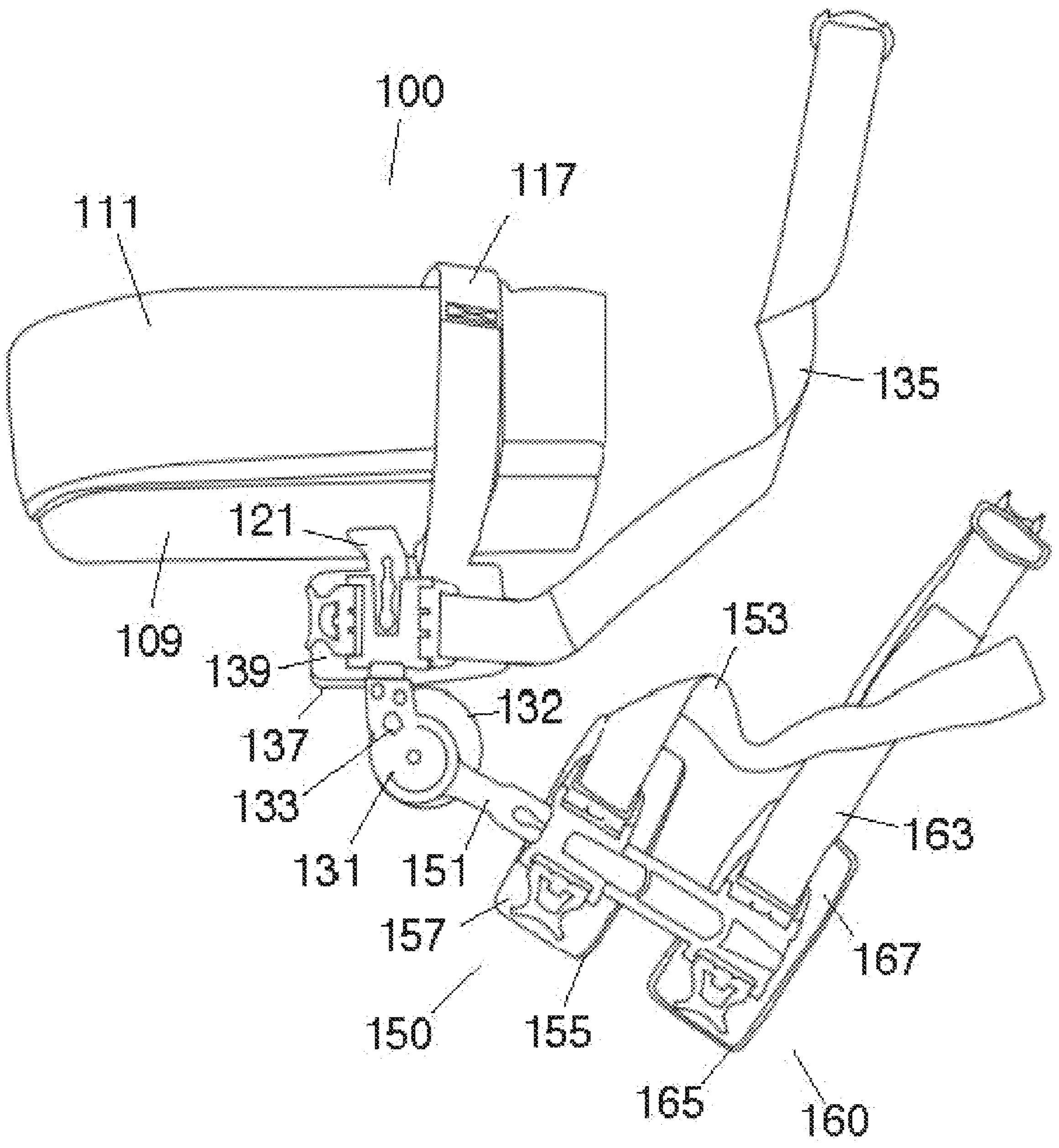
FIG. 3 illustrates a left side view of an embodiment of a right arm support with the hinge rotated.

With reference to FIGS. 1, 2, and 3, the present invention is directed towards an improved arm brace 100 for supporting the injured arm that is not supported by the patient's neck and can allow the hand supported by the brace 100 to perform functional tasks. In the illustrated embodiment, the arm brace 100 includes an arm pad 111 mounted to an upper surface of an arm support platform 109. The arm pad 111 can be made of a foam material that is covered with an elastic fabric. In an embodiment, the arm support platform 109 can be a planar structure that provides support for the entire lower planar surface of the arm pad 111. In other embodiments, the arm pad 111 and the arm support platform 109 can be any other suitable structures and shapes that can support and protect the patient's arm.

The arm pad 111 can be a thick structure that has substantially vertical side walls and planar top and bottom surfaces. The arm pad 111 can have a slot 113 that can have a shape that roughly matches the shape of the patient's forearm. When the brace 100 is worn, the forearm can be placed into the slot 113. The elbow end of the slot 113 can be closed and the hand end of the slot 113 can be opened so that the hand and fingers can extend out from the hand end of the arm pad 111. This opening can allow the hand to extend out from arm brace 100 and be positioned so that the hand can be used for various tasks such as grasping items, writing, drawing, typing, etc. The slot 113 can have a "U" shaped cross section and can be shaped and contoured to support the user's forearm.

The hand end of the arm pad 111 can have detachable foam pieces that can be removed to allow the length of the slot 113 to be adjusted to properly fit the patient's forearm. A long forearm may properly fit the unmodified slot 113 in the arm pad 111. However, if the patient has a short forearm, the hand may not extend out of the open hand end of the slot 113. The arm pad 111 can have customizable features that allow it to fit a wide variety of users. For example, the arm pad 111 can have detachable pieces that can be removed so that the slot 113 of the arm pad 111 can be easily shortened to provide a proper fit.

One or more arm straps 117 can be wrapped around the arm pad 111 and the arm support platform 109 to help secure the forearm to the arm brace 100. The arm strap 117 can prevent the patient from accidentally lifting the arm out of the arm brace 100. Accidentally removing the forearm from the slot 113 of the arm pad 111 can result in a loss of protection and support and may result in injury to the limb.

The arm support platform 109 can be coupled to an upper portion of an upper support structure 121. In the illustrated embodiment, the upper support structure 121 can be an inverted "L" shaped adjustable bracket having a horizontal elongated member that can be rigidly secured to the lower surface of the arm support platform 109 and a vertical elongated member. In an embodiment, the arm support platform 109 can be rotated to any desired position on the upper portion of the upper support structure 121. For example, the arm support platform 109 can be coupled to the upper portion of the upper support structure 121 with a swivel or rotational mechanism. In an embodiment, the rotational mechanism can be a bolt or screw 122 in a vertical orientation. The bolt or screw 122 can be loosened and the arm support platform 109 can be rotated to the desired position. The bolt or screw 122 can then be tightened to secure the arm support platform 109 at the desired rotational position to the upper portion of the upper support structure 121. Additional screws can be used to further secure the arm support platform 109 to the upper portion of the upper support structure 121.

The lower portion of the upper support structure 121 can be coupled to a waist pad 137 and a waist strap 135 that is attached around the waist of the patient. A lower end of the upper support structure 121 can be coupled to an upper portion of a hip hinge 131 that can provide angular rotational support to the arm support platform 109.

As discussed, the upper support structure 121 can be an inverted "L" bracket that is formed from two elongated members that can be perpendicular to each other. Both the upper portion and the lower portion elongated members of the support structure 121 can be extendable and retractable in length. These adjustable length features can allow the arm brace 100 to be adjusted to properly fit a wide variety of patients and allow the brace supported forearm to be positioned as desired by the patient or the patient's doctor. The lower portion of the upper support structure 121 can be vertically oriented and lengthened to properly fit tall patients or shortened for shorter patients. The lower portion of the upper support structure 121 can have a locking mechanism that can be used to lock the elongated structures to any desired length. For example, the elongated members can have proximal and distal portions that are secured to each other with fasteners such as screws. After the elongated members are adjusted to the desired lengths and positions, the screws can be tightened to lock the lengths of the elongated members.

As discussed, the upper portion of the upper support structure 121 is coupled to the arm support platform 109. The upper portion of the upper support structure 121 can be an elongated structure that can be horizontally oriented and can be adjustable in length to adjust the position of the supported arm pad 111. When the arm support platform 109 and the arm pad 111 need to be close to the patient, the length of the upper portion of the upper support structure 121 can be locked in a short extension. If the arm needs to be moved and/or angled away from the patient's torso the upper support structure 121 can be horizontally extended to move the arm support platform 109 away from the body. This arm position away from the patient can be useful if the hand needs to perform functions such as typing, writing, drawing, touch interactions with a user interface screen, etc.

The arm brace 100 can be coupled to a waist strap assembly that includes a waist pad 137, a support plate 139, and a waist strap 135. The waist pad 137 can be made of a soft elastic material such as foam and can have a concave cylindrical surface that can be placed against the waist of the user. A support plate 139 can be coupled to the outer convex surface of the waist pad 137. The support plate 139 can be a curved rigid structure that can distribute pressure across the entire area of the waist pad 137. The waist strap 135 can be placed against the outer convex surface of the support plate 139 so that when the waist strap 135 is tightened, the support plate 139 will compress the support plate 139 and the waist pad 137 against the patient. The waist strap 135 can be wrapped around the waist and positioned above the hips of the patient. An end of the waist strap 135 can be secured to a coupling mechanism such as a buckle, a hook/loop coupling mechanism or any other suitable fastener to the opposite end of the waist strap 135. Once the waist strap 135 is around the patient, the waist strap 135 can be tightened so that the waist pad 137 is compressed against the torso of the patient. The waist strap 135 just above the hips of the patient can provide support for the arm brace 100 similar to the waist strap of a backpack.

The hinge 131 is coupled to the upper support structure 121 and a lower support structure 151. The hinge 131 can have an axis of rotation that is substantially horizontal. The hinge 131 can be placed adjacent to the patient's hip and positioned with the axis of rotation aligned with the axis rotation of the patient's hip. The hinge 131 can allow the patient's leg to rotated relative to the torso so that the arm brace 100 continues to be fully supported when the patient is standing, sitting, walking, or moving. The hinge 131 can be a thin disc shaped structure with a smooth flat surface that is faces the patient. A hinge pad 132 can be placed against hinge 131 so that the hinge pad 132 is in contact with the patient. The hinge pad 132 can be made of a soft elastic material such as elastic foam for patient comfort and to avoid abrasion.

In some embodiments, the hinge 131 can have rotation limiting controls 133 that can be used to prevent or limit the rotation of the lower support structure 151 relative to the upper support structure 121. The rotation limiting controls 133 can be used to protect the user from over rotation of the hip joint. For example, the rotation limiting controls 133 can limit the hinge rotation between 180 degrees and 90 degrees so that the user can stand with the hinge at 180 degrees and then sit with the hinge at 90 degrees. The rotation limits can prevent the leg from being rotated backwards out of vertical alignment or into an excessive seated hip bend. In other embodiments, the rotation limiting controls 133 can allow any other rotational range or the rotation limiting controls 133 can lock the hip at a specific angular orientation.

The lower support structure 151 can be an elongated structure that is coupled to the user's leg with a first assembly 150 and a second leg strap assembly 160. In the illustrated embodiment, the first leg strap assembly 150 has a first leg strap 153, a first leg pad 155, and a first leg support plate 157. The second leg strap assembly 160 has a second leg strap 163, a second leg pad 165, and a second leg support plate 167. The leg straps 153, 163 can be wrapped around the leg and tightened to compress the support plates 157, 167 and the leg pads 155, 165 against the thigh of the patient. In some embodiments, the length of the lower support structure 151 can be adjustable so that it properly fits the patient. When the lower support structure 151 is coupled to the patient's thigh, the brace 100 has increased angular stabilization for the arm platform 109 and the arm pad 111.

With reference to FIG. 3, the brace 100 is illustrated with the hinge 131 partially rotated and the lower support structure 151 out of alignment with the upper support structure 121. The lower support structure 151 is secured to the leg and when the user's leg rotates about the hip joint, the hinge 131 allows the lower support structure 151 to move while the arm support platform 109 and arm pad 111 can remain in a substantially horizontal orientation. Thus, the arm brace 100 can bend at the hinge 131 so the user can sit down while maintaining vertical and angular support for the arm platform and the arm pad 111. This feature is very important for user functionality since the user can walk, sit, stand, or move much freely without compromising the support provided by the brace to the arm.

Figure 4:
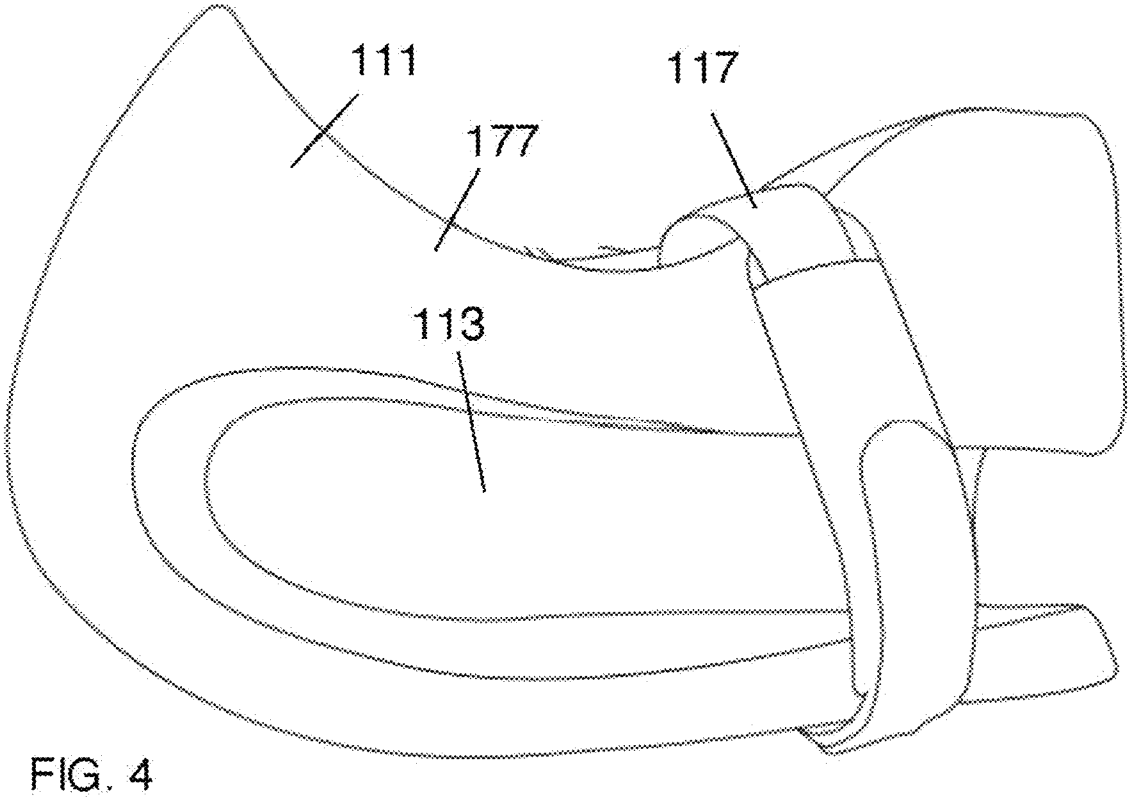
FIG. 4 illustrates a top view of an embodiment of a right arm pad.

With reference to FIG. 4, a top view of an embodiment of a right arm pad 111. The arm pad 111 can include a soft elastic foam pad structure that is covered with a soft elastic fabric material cover 177. The foam can be formed to the outer shape of the arm pad 111 and placed within a pocket of the fabric cover 177. The fabric cover 177 can have an internal pocket that has an internal volume that roughly matches the outer surfaces of the foam padding. The foam pad structure can tightly fit within the internal pocket of the fabric cover 177. The elastic fabric cover 177 can be made of materials such as Lycra, Spandex, or other breathable soft elastic materials. Thus, the fabric cover 177 can stretch around the foam pad so that if the user reduces or alters the size of the foam padding, the elastic fabric cover will contract and still fit tightly over the revised foam pad structure.

In the illustrated embodiment, the arm pad 111 has vertical external side surfaces, so that the arm pad has a rectangular cross section shape. In other embodiments, the arm pad 111 can have rounded convex side wall shapes or any other suitable side wall shape. The external side surface of the arm pad 111 that is adjacent to the patient can be concave and cylindrical in shape that can match the outer surface of the patient's torso. As discussed, the arm pad 111 is placed on the support platform. The concave portion of the arm pad 111 can extend over the edge of the support platform so that the support platform never comes into contact with the torso of the patient even if the concave portion of the arm pad 111 is compressed against the patient.

In the illustrated embodiment, the arm is placed in the arm slot 113. The elbow end of the slot 113 can be padded while the hand or wrist end of the slot 113 can be opened to allow the patient's hand to extend out of the arm pad 111. The illustrated slot 113 has vertical side walls and a flat lower surface. Additional pads can be placed against the side and/or lower surfaces of the slot 113 to improve the comfort or increase the immobilization of the forearm. In other embodiments, the cross section of the slot 113 can be any other shape such as "U" shaped rather than a rectangular cross section shape. The arm pads 111 illustrated is the figures are used for right arms. If a left arm was injured, the arm pad 111 would be a mirror image with the concave side of the arm pad 111 on the opposite side.

In some embodiments, the arm pad 111 can be made from elastic foam such as open or closed cell foam rubber or memory foam. The open cell foam can provide more ventilation to the forearm, while the closed cell foam can provide more insulation. In some embodiments, the arm pad 112 can be easily customized to fit different sized patient forearms. For example, the foam pad 171 can initially be very long in length so that it will be large enough to fit patients having large forearms. If the foam pad 171 is used by a user with a large forearm, then no modification is required. However, if the patient's forearm is shorter and the arm pad 171 is too long, then the foam arm pad 171 can be cut and reduced in length to match the length of the patient's forearm.

In an embodiment, the hand end of the foam pad 171 can have a plurality of serrations 173 through the width of the foam pad 171 that provide cut or tear away portions at the hand end. Small portions of the foam pad 171 can be removed at the serrations 173 to make the length of the foam pad 171 shorter. The user can measure their forearm and then cut or tear the arm pad 171 at the serration 173 to adjust the length of the foam pad 171 to match the measured length of the patient's forearm. Once the size is adjusted, the foam pad 171 can be placed back into the pocket of the elastic fabric cover that can be adjusted to fit tightly over the foam arm pad.

Figure 5:
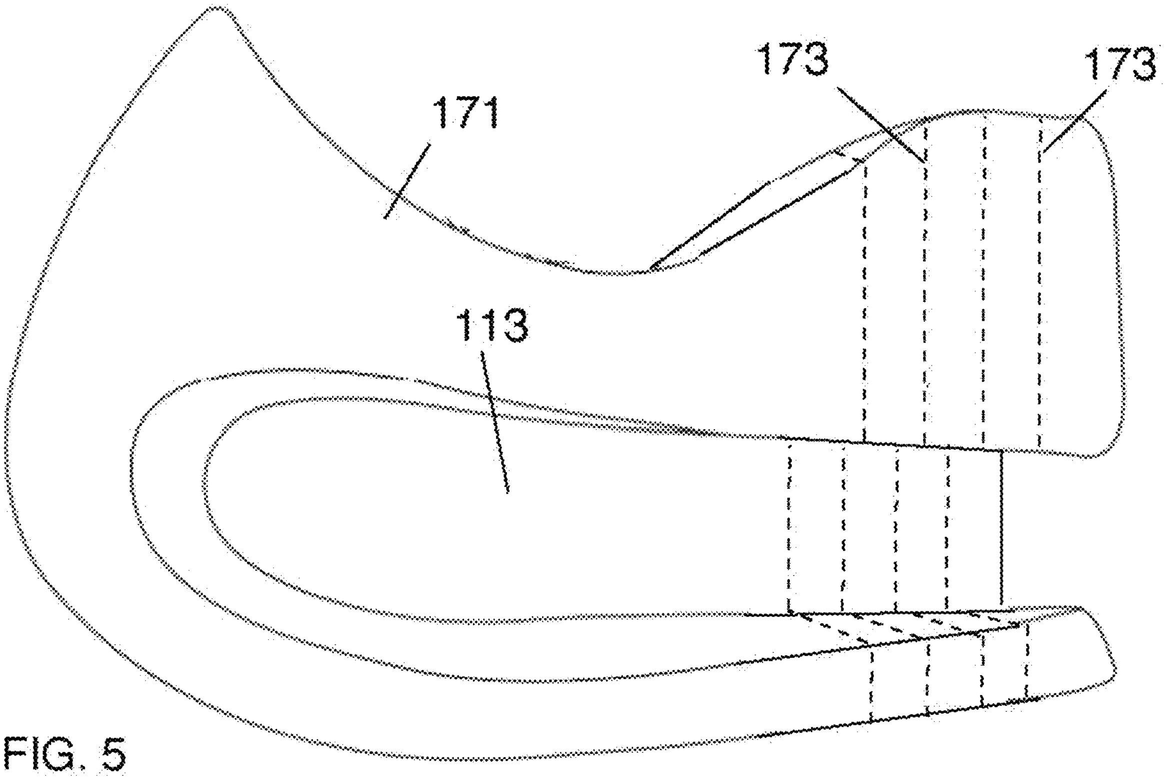
FIG. 5 illustrates a top view of an embodiment of a right arm pad.
Figure 15:
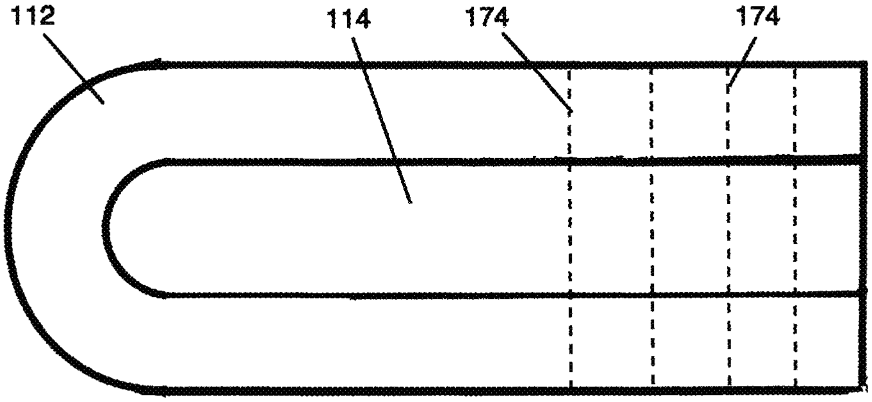
FIG. 15 illustrates a top view of an embodiment of a universal arm pad.
Figure 16:
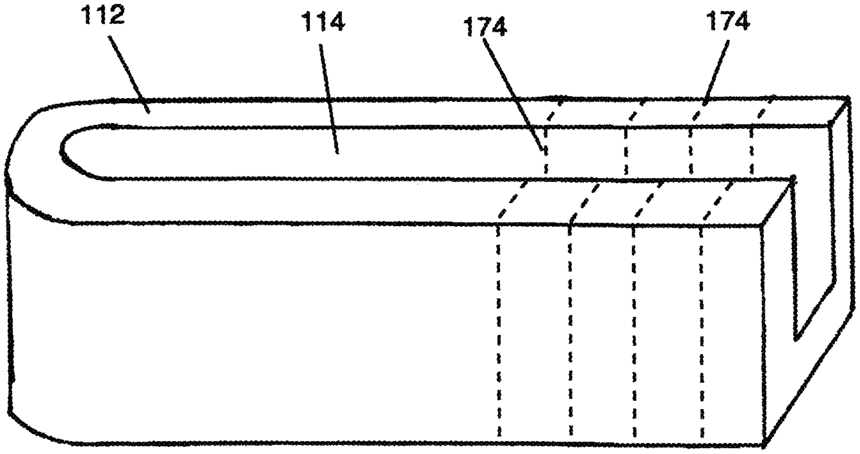
FIG. 16 illustrates a top perspective view of an embodiment of a universal arm pad.

FIG. 15 illustrates a top view and FIG. 16 illustrates a top perspective view of an embodiment of a universal arm pad 112 that is symmetric and can be used for either a left or a right arm. The illustrated universal symmetric arm pad 112 can be placed on the described arm support platform and used instead of the right arm pad illustrated in FIGS. 4 and 5. The arm pad 112 can include a soft elastic foam pad structure that is covered with a soft elastic fabric material cover. The arm pad 112 can be placed within a pocket of the fabric cover. The fabric cover can have an internal pocket that has an internal volume that roughly matches the outer surfaces of the arm pad 112. The arm pad 112 can tightly fit within the internal pocket of the fabric cover. The elastic fabric cover can be made of materials such as Lycra, Spandex, or other breathable soft elastic materials that can stretch around the arm pad 112 so that if the user reduces or alters the size of the foam padding, the elastic fabric cover will contract and still fit tightly over the revised arm pad 112.

The arm pad 112 can be made from elastic foam such as open or closed cell foam rubber or memory foam. The open cell foam can provide more ventilation to the forearm, while the closed cell foam can provide more insulation. In some embodiments, the arm pad 112 can be easily customized to fit different sized patient forearms. For example, the foam arm pad 112 can initially be very long in length so that it will be large enough to fit patients having large forearms. If the arm pad 112 is used by a user with a large forearm, then no modification is required. However, if the patient's forearms is shorter and the arm pad 112 is too long, then the arm pad 112 can be cut and reduced in length to match the length of the patient's forearm.

In an embodiment, the hand end of the arm pad 112 can have a plurality of serrations 174 through the width of the arm pad 112 that provide cut or tear away portions at the hand end. Small portions of the foam pad 172 can be removed at the serrations 174 to make the length of the arm pad 112 shorter. The user can measure their forearm and then cut or tear the arm pad 172 at the serration 174 to adjust the length of the arm pad 112 to match the measured length of the patient's forearm. Once the size is adjusted, the arm pad 112 can be placed back into the pocket of the elastic fabric cover that can be adjusted to fit tightly over the foam arm pad.

In the illustrated embodiment, the right or left arm can be placed in the arm slot 114. The elbow end of the slot 114 can be closed and padded while the hand or wrist end of the slot 114 can be opened to allow the patient's hand to extend out of the arm pad 112. The illustrated slot 114 has vertical side walls and a flat lower surface. Additional pads can be placed against the side and/or lower surfaces of the slot 114 to improve the comfort or increase the immobilization of the forearm. In other embodiments, the cross section of the slot 114 can be any other shape such as "U" shaped rather than a rectangular cross section shape. Because the arm pad 112 can be used for both left and right arms and are adjustable in length, this single arm pad 112 design can be used for all patients who need an arm brace.

Figure 6:
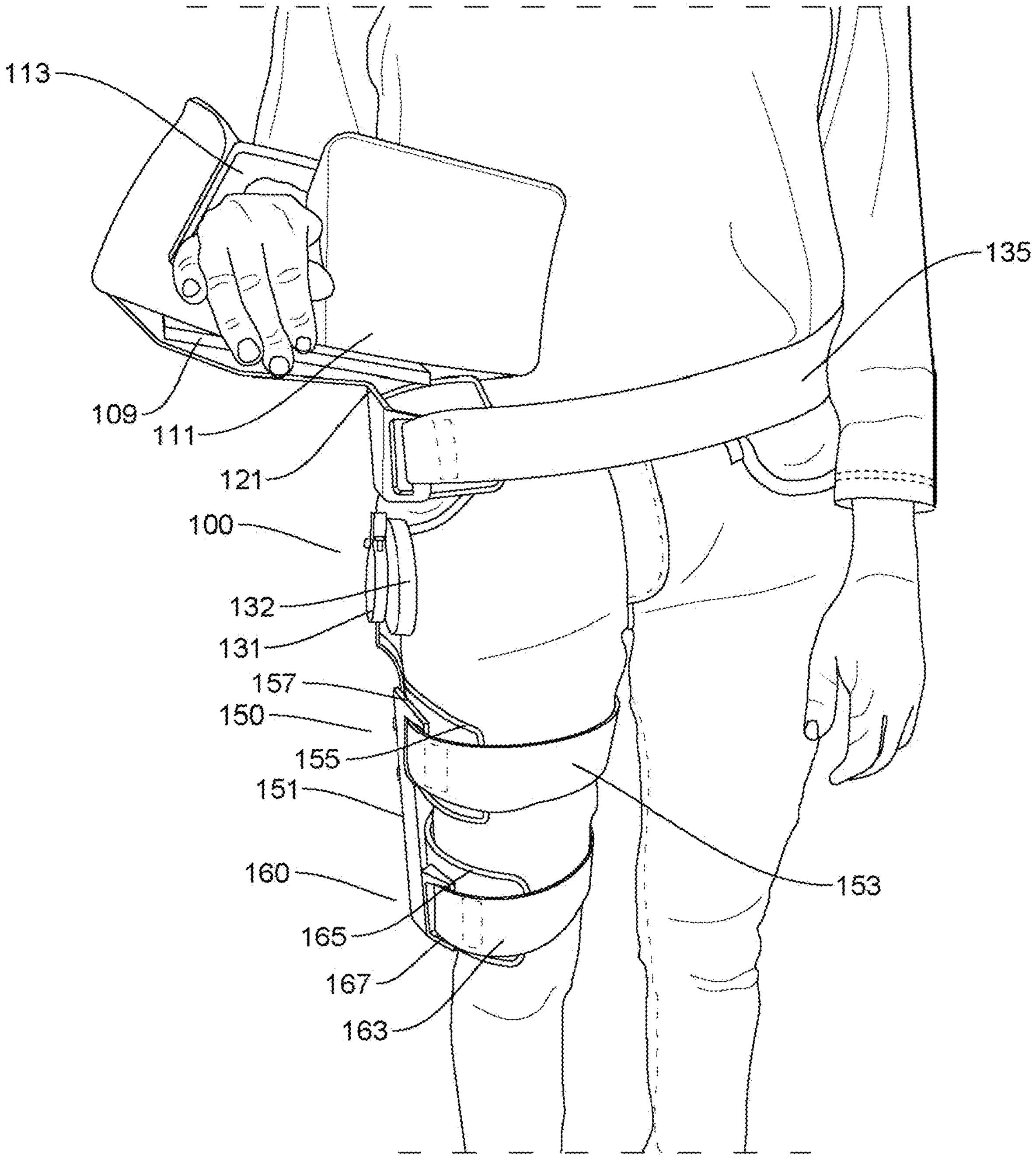
FIG. 6 illustrates a front view of a patient wearing an embodiment of the arm brace.
Figure 7:
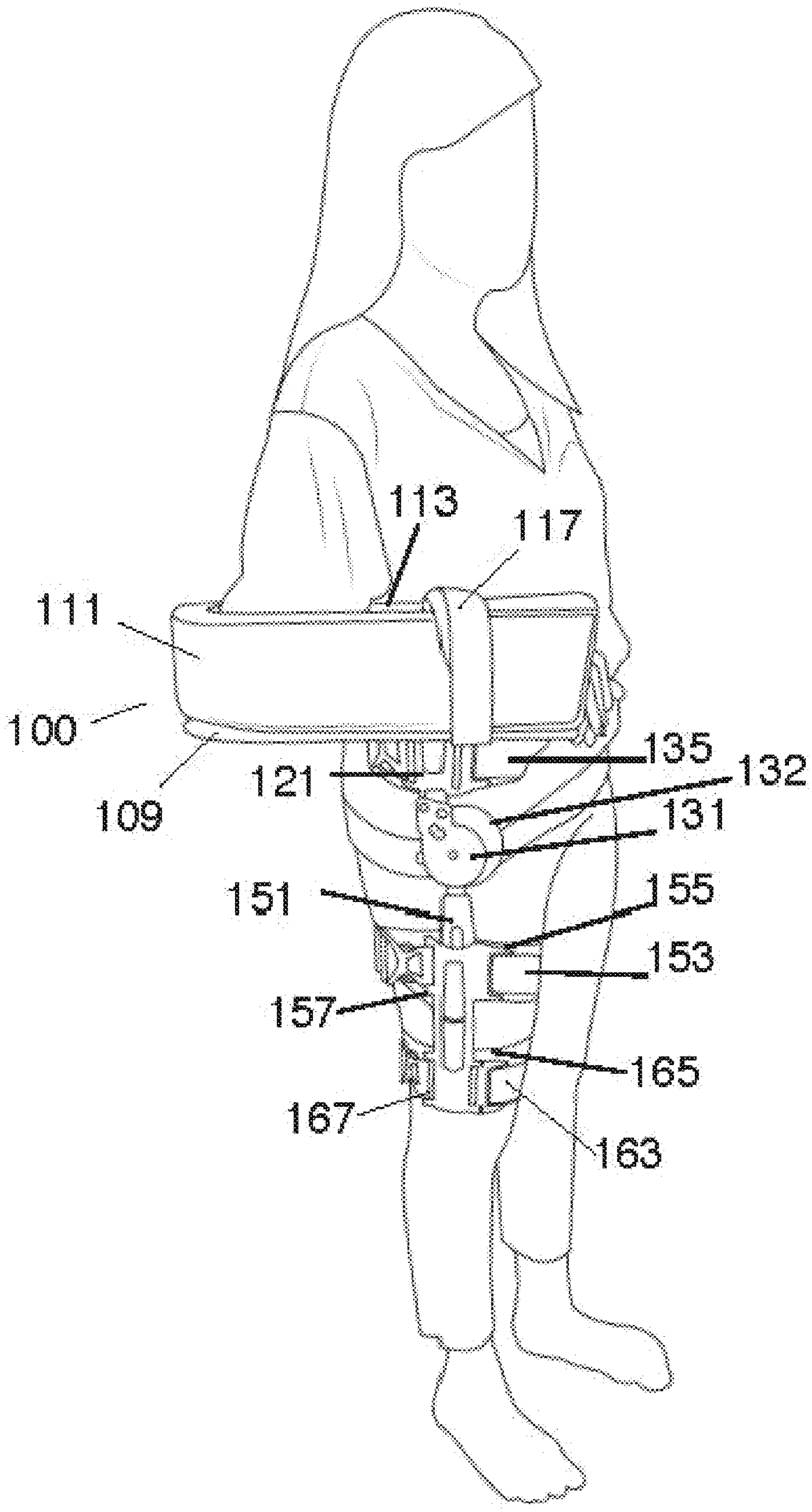
FIG. 7 illustrates a side view of a patient wearing an embodiment of the arm brace.
Figure 8:
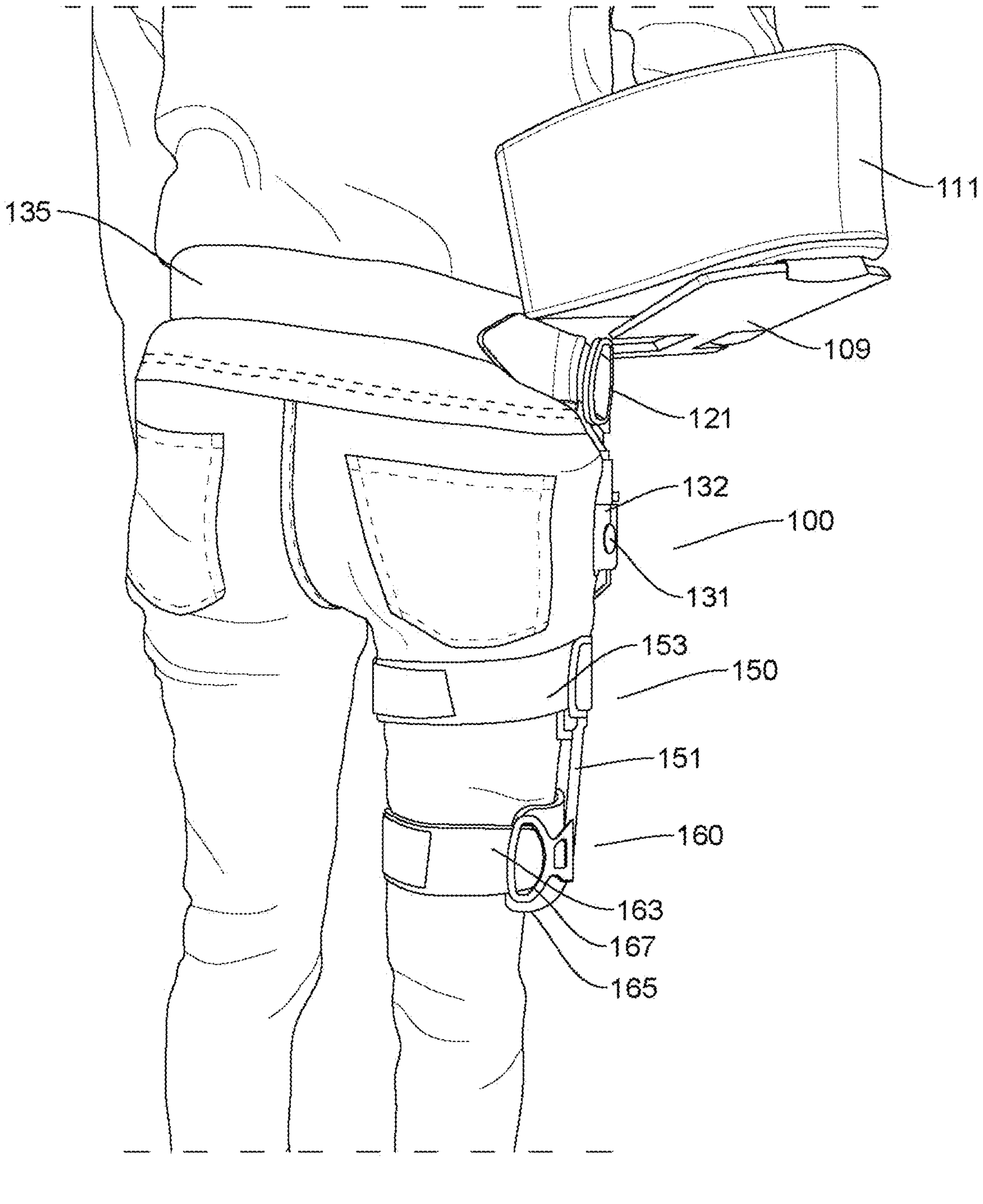
FIG. 8 illustrates a rear view of a patient wearing an embodiment of the arm brace.

FIG. 6 is a front view, FIG. 7 is a side view, and FIG. 8 is a rear view of a patient wearing an embodiment of the arm brace 100. The patient's arm is placed in the slot 113 of the arm pad 111 that rests on the arm support platform 109. The bottom of the arm support platform 109 is attached to an upper support structure 121. In the illustrated embodiment, the upper support structure 121 has an inverted "L" shaped adjustable bracket which can have adjustable features that allow the position of the arm support platform 109 on the upper horizontal portion of the support structure 121 to be adjusted. This allows the user to move the horizontal position of the arm pad 111 relative to the upper support structure 121 so the arm pad 111 and arm slot 113 can be moved to a comfortable or functional position. The arm brace 100 can be configured to hold the forearm adjacent to and across the patient's torso or alternatively, the arm brace 100 can be configured to hold the forearm away from the patient's torso across with the hand end of the arm slot 113 facing away from the patient's torso.

In the illustrated embodiment, the upper portion of the upper support structure 121 bracket is a horizontal structure that can have a center slot that extends along the length. Screws or bolts can be placed through the slot and holes in the arm support platform 109. This confirmation can allow the user to adjust the position of the arm support platform 109 on the upper portion of the upper support structure 121 bracket. The screws or bolts can be tightened, when the arm support platform 109 is properly positioned on the upper portion of the upper support structure 121 bracket to lock the arm support platform 109 in place.

The lower portion of the upper support structure 121 bracket can be coupled to the upper portion of the hinge 131. A waist strap 135, a waist pad 137, and a waist support plate 139 can also be coupled to the lower portion of the upper support structure 121 bracket. The waist pad 137 is made of a soft elastic material. The inner surface of the waist pad 137 is placed against the waist of the patient and the outer surface of the waist pad 137 can be placed against the waist support plate 139 that can be coupled to the lower portion of the upper support structure 121 bracket. The waist strap 135 is wrapped around the waist of the patient and when tightened the waist strap 135 can compress the waist pad 137 and the waist support plate 139 against the waist of the patient. The waist strap 135 can function like a hip belt of a backpack and provide most of the vertical support for the arm brace 100 and the patient's arm.

The vertical elongated member that is the lower portion of the upper support structure 121 bracket can also be adjustable in length. In an embodiment, the lower portion of the upper support structure 121 bracket can have two elongated pieces that are coupled together with screw fasteners. The screw fasteners can be loosened to allow the vertical length of the upper support structure 121, the support plate 139, and the arm pad 111 to be moved to the desired vertical position to provide vertical support to the patient's forearm. The screw fasteners can then be tightened to lock the arm pad 111 at the desired vertical position.

In other embodiments, any other length adjustment mechanism can be used to adjust the horizontal and vertical lengths of the upper support structure 121 and control the position of the bracket support plate 139 and the arm pad 111. For example, the horizontal and vertical members of the upper support structure 121 bracket can be telescoping structures that can have concentric cylindrical poles with a length locking mechanism. The locking mechanism can be released to extend the lengths of the horizontal and vertical members to position the arm pad 111 at the desired horizontal and vertical positions. In some embodiments, the locking mechanism can be a quick release type clamp that can very easily be locked and released. This telescopic mechanism with quick release lever locks can be useful to allow a user to quickly and easily adjust the arm pad 111 to desired position. These types of quick release adjustments can allow easier adjustments than having to loosen fasteners, adjusting the extensions and then tightening screw type fasteners.

The hinge 131 is attached to the lower support structure 151 that can be an adjustable length elongated structure that extends down the outer side of the patient's right leg in a parallel orientation. The middle portion of the lower support structure 151 can be attached to a first leg strap assembly 150 and the lower end of the lower support structure 151 can be attached a second leg strap assembly 160. The first leg strap assembly 150 can include a first leg pad 157, a first leg support plate 159, and a first leg strap 155. The second leg strap assembly 160 can include a second leg pad 167, a second leg support plate 169, and a second leg strap 165. The leg straps 155, 165 can be tightened around the thigh of the patient to compress the leg pads 157, 167 and the support plates 159, 169 against the leg. The hinge 131 and lower support structure 151 can provide vertical stability to the arm pad 111 and support plate 139 so the patient's arm is securely supported and protected by the brace 100.

The length of the lower support structure 151 can be adjusted so that the leg straps 155, 165 are positioned at comfortable locations on the leg. When the length of the lower support structure 151 is adjusted to the desired length, the screw fasteners can be tightened to lock the lower support structure 151 at the desired length. In other embodiments, any other length adjustable structures can be used such as telescoping concentric cylinders with a locking mechanism as described above.

Figure 9:
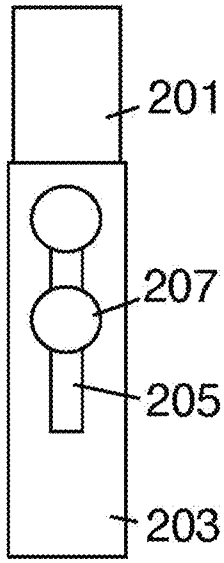
FIG. 9 illustrates a front view of an embodiment of an adjustable length member in an extended position.
Figure 10:
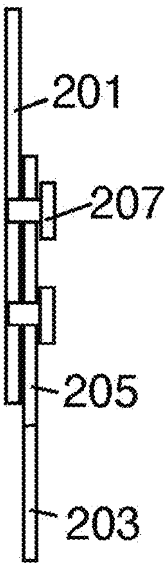
FIG. 10 illustrates a side view of an embodiment of an adjustable length member in an extended position.
Figure 11:
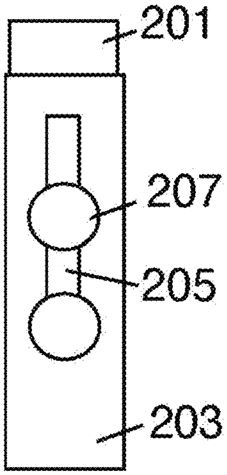
FIG. 11 illustrates a front view of an embodiment of an adjustable length member in a retracted position.
Figure 12:
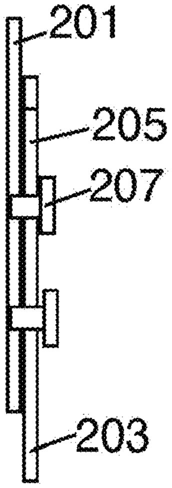
FIG. 12 illustrates a side view of an embodiment of an adjustable length member in a retracted position.

As discussed, the upper support structure 121 and the lower support structure 151 can have elongated components that can be adjustable in length. Examples of possible adjustable length structures are illustrated in FIGS. 9-14. FIGS. 9-12 illustrates an embodiment of the adjustable length structure that is made from two flat elongated pieces 201, 203. FIGS. 9 and 10 illustrate the adjustable length structure in a lengthened configuration and FIGS. 11 and 12 illustrate the adjustable length structure in a compressed configuration.

In the first illustrated embodiment shown in FIGS. 9-12, the elongated structure can include two elongated rigid structure 201, 203 that slides against each other while the length is being adjusted. The lower structure 203 can have a slot 205 that extend along the length and the upper structure 201 can have threaded screw holes. Screw fasteners 207 can be placed through the slot 205 and screwed into the upper structure 201. The screw fasteners 207 can be loosened to adjust the length of the elongated structure and tightened to lock the length of the elongated structures.

Figure 13:
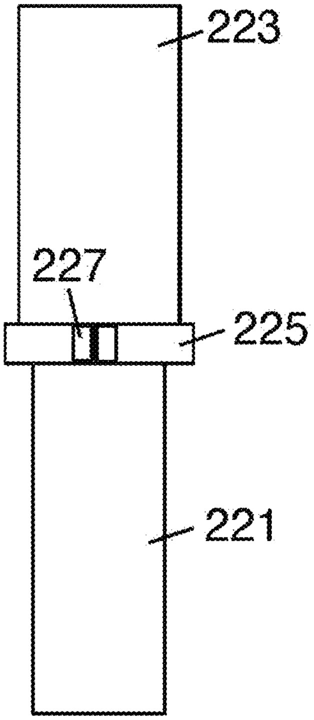
FIG. 13 illustrates a front view of a concentric tubular embodiment of an adjustable length member.
Figure 14:
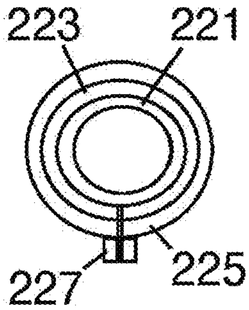
FIG. 14 illustrates an end view of a concentric tubular embodiment of an adjustable length member.

In a second illustrated embodiment shown in FIGS. 13 and 14, the elongated structure can include an inner tube 221 and an outer tube 223 that are in a concentric telescopic configuration. A clamping ring 225 and a clamping mechanism 227 is attached to an end of the outer tube 223 that the inner tube 221 extends out of. The clamping mechanism 227 can be loosened to allow the inner tube 221 to slide within the outer tube 223. When the tubular elongated structure is adjusted to the desired length, the clamping mechanism 227 can be tightened to rigidly secure the inner tube 221 to the outer tube 223. The clamping mechanism 227 can be screw coupling, a quick release lever cam, or any other suitable clamping mechanism. The illustrated elongated structure uses circular cross section tubes. In other embodiments, the tubes can have any other cross section shape such as square, rectangular, oval, triangular, or other geometric shapes that can allow concentric sliding movement of the tubes. In other embodiments, the inventive arm brace can use any other type of adjustable elongated structure so that the arm brace can be adjusted to fit various patients and provide a wide range of arm positions.

Figure 17:
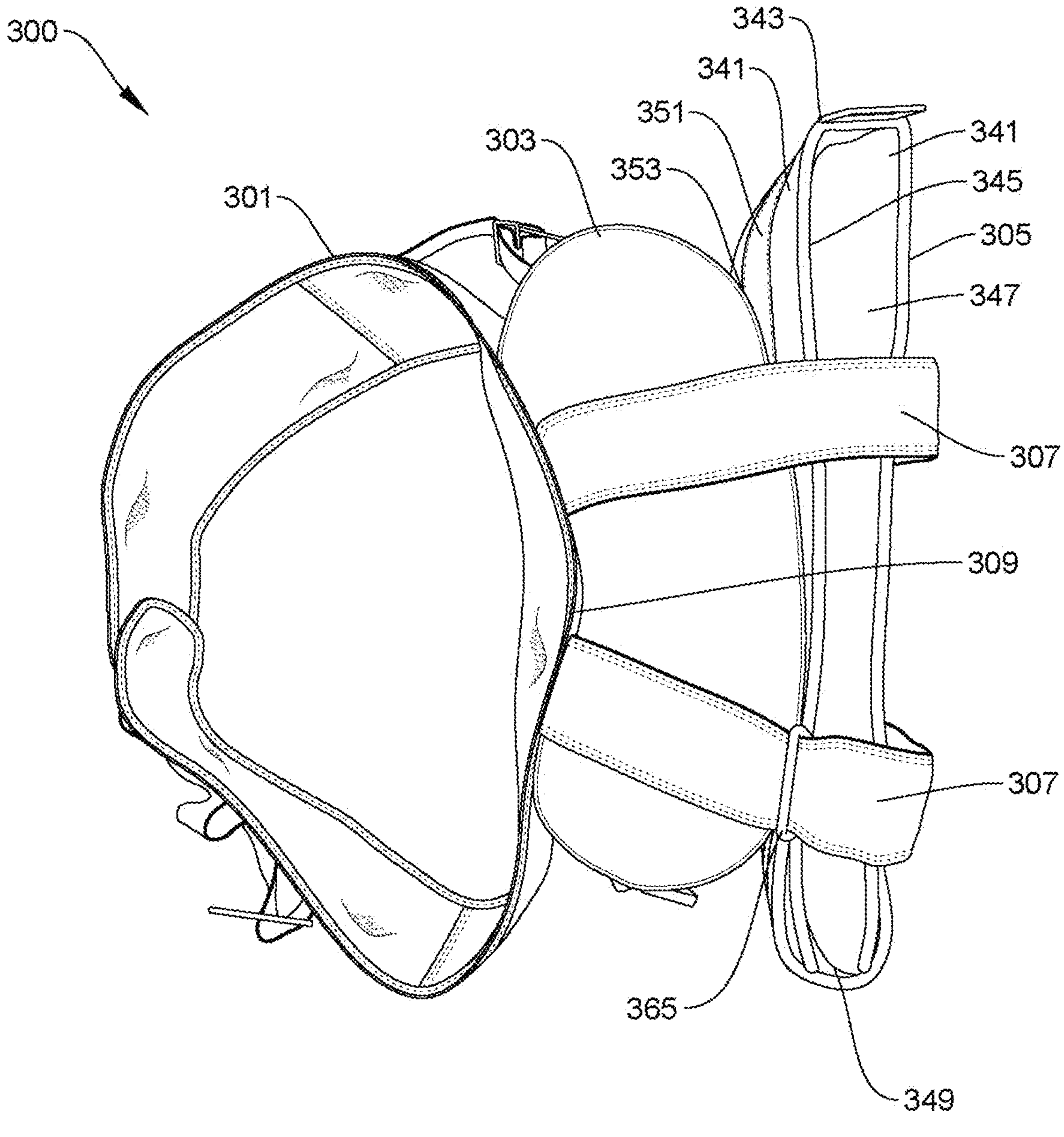
FIG. 17 illustrates a top view of an embodiment of the arm brace.

FIG. 17 illustrates a top view of another embodiment of the arm brace. The arm brace 300 can comprise a wrap member 301, an arm support member 303, an arm sleeve member 305, and straps 307 that can secure the arm sleeve member 305 to the arm support member 303 and the wrap member 301. The wrap member 301 can be an elongated flexible structure that is placed around the waist of a user. The ends of the wrap member 301 can be secured to each other with a coupling mechanism to hold the wrap member 301 in place on the user's waist. In some embodiments, the coupling mechanism can be a hook material on one end portion of the wrap member 301 and a loop material on an opposite end portion of the wrap member 301. In other embodiments, any other suitable coupling mechanism can be used.

In some embodiments, the arm support member 303 can be made of a soft compressible material that can be covered with a fabric or other protective material. The arm support member 303 can be elongated to provide sufficient outer surface areas to support the forearm of the user. The arm support member 303 can have a concave cylindrical surface that can roughly match the curvature of a user's waist, rounded convex ends, and a convex outer surface. The lower surfaces of the arm support member 303 can be a planar surface. The upper surface of the arm support member 303 can be a planar surface or a straight concave surface that can extend along the length of the arm support member 303.

The arm sleeve member 305 can be adapted to surround the forearm of the patient. The arm sleeve member 305 can be detachably coupled to the arm support member 303. In some embodiments, the arm brace 300 can have an arm strap 307 to further secure the arm sleeve member 305 to the arm support member 303. In the embodiment illustrated in FIG. 17, there are two arm straps 307. It can be understood that there can be any number of arm straps, one arm strap or more than two arm straps.

The arm sleeve member 305 can be a fabric structure that has a "U" shaped cross section that the arm can rest within. The arm sleeve member 305 can have two side walls 341 on opposite sides of a bottom 345 portion, and a rear end wall 343 where the elbow can rest. The front of the arm sleeve member 305 can be an open end so that the hand can extend out of the arm sleeve member 305. A fastener 351 strip such as a hook strip can be attached to the outer sidewall 341 of the arm sleeve member 305 that can be coupled to a loop outer surface of the support member 303. In the illustrated configuration, the arm sleeve member 305 is attached to the outer convex surface of the arm support member 303. In other embodiments, the arm sleeve member 305 can be attached to the top surface of the arm support member 303.

Figure 19:
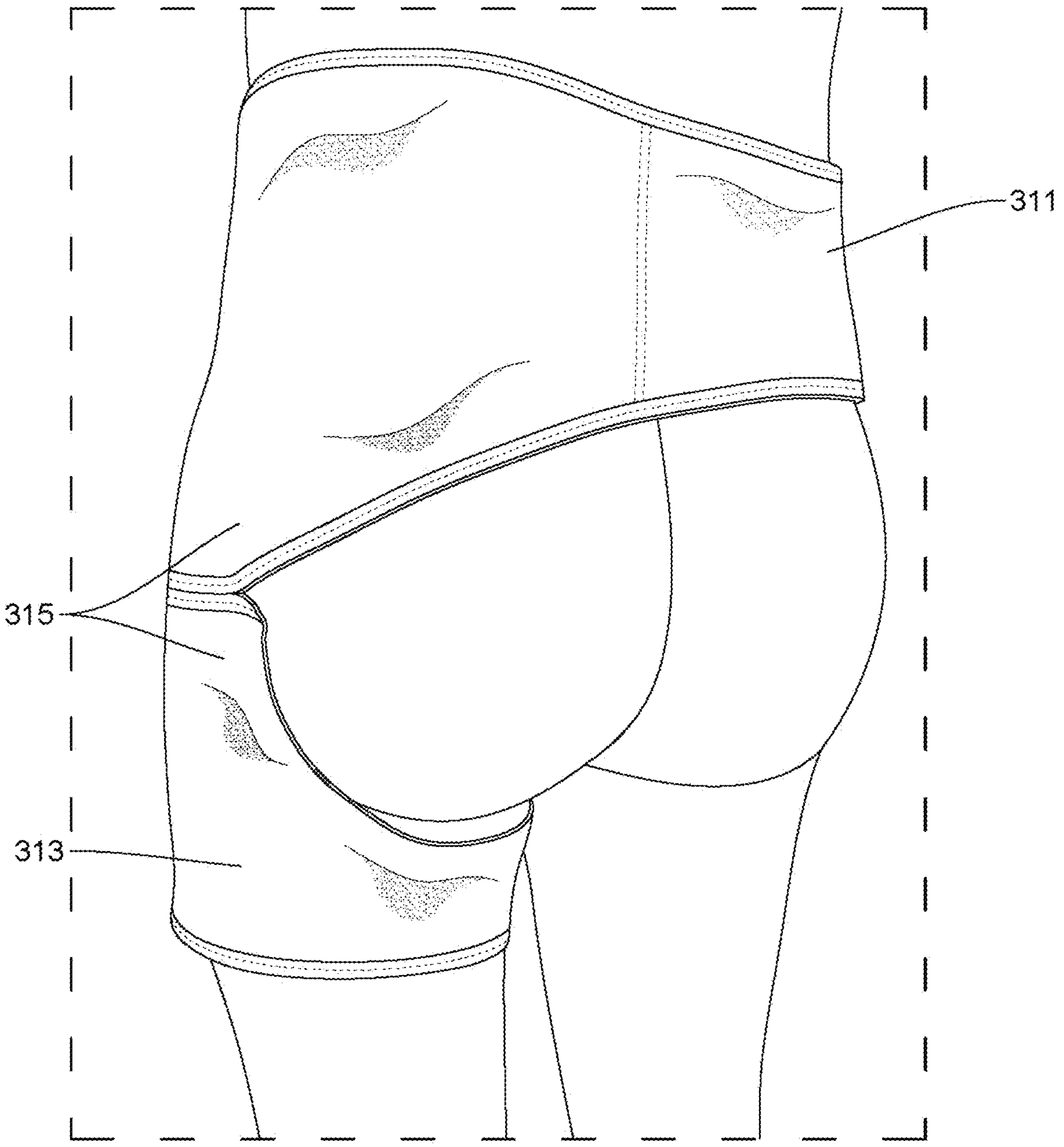
FIG. 19 illustrates a rear perspective view of a patient wearing an embodiment of a wrap member of the arm brace.
Figure 20:
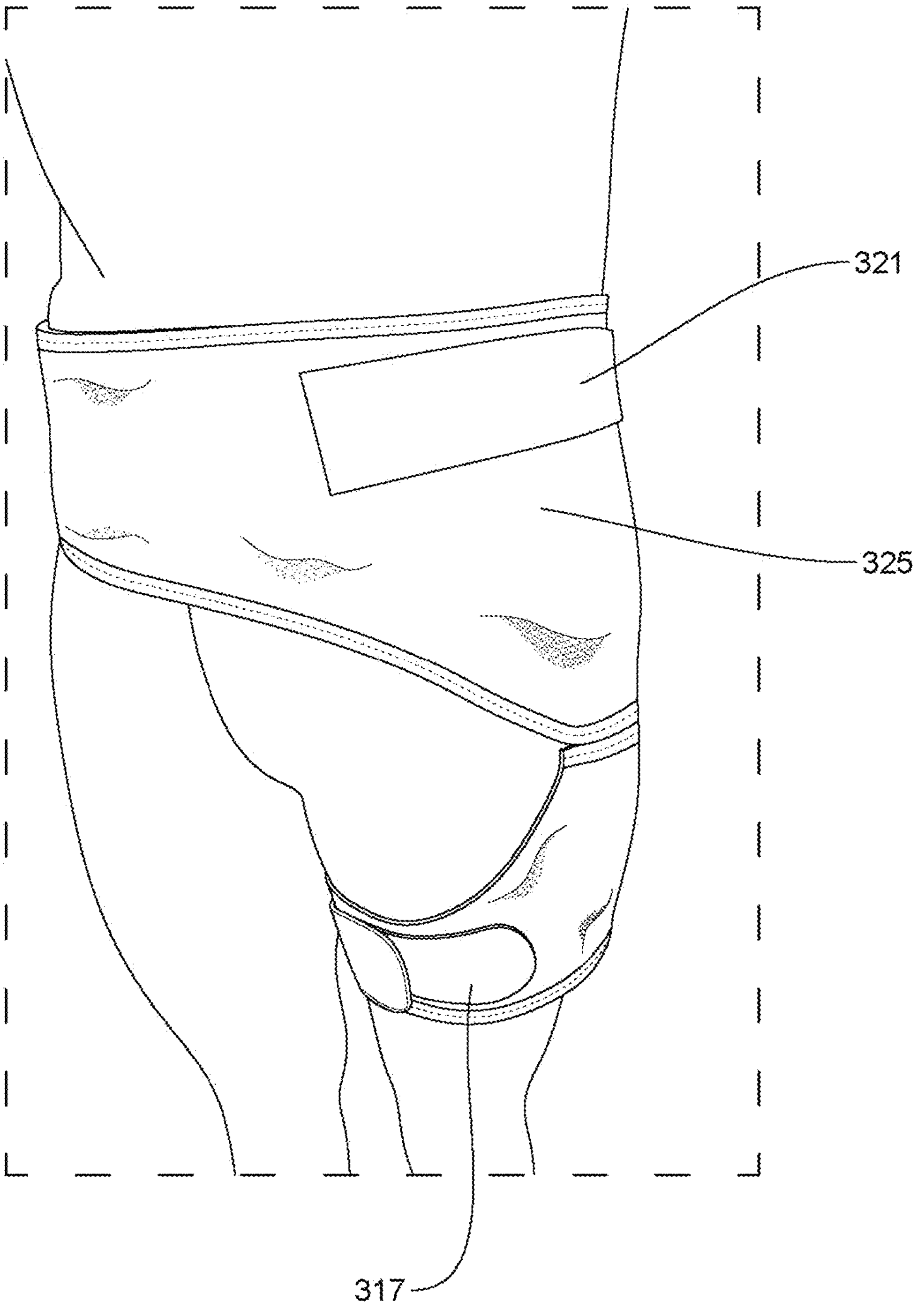
FIG. 20 illustrates a front perspective view of a patient wearing an embodiment of a wrap member of the arm brace.

The wrap member 301 can have a waist wrap piece 311 that wraps around the waist and a thigh wrap piece 313 that wraps around the thigh of a patient as shown in FIGS. 19 and 20. The waist wrap piece 311 can be coupled to the thigh wrap piece 313. When the thigh wrap piece 313 is secured around the thigh, it can prevent the waist wrap piece 311 from sliding around the waist of the user that can provide a more stable arm support member 303 position.

Figure 25:
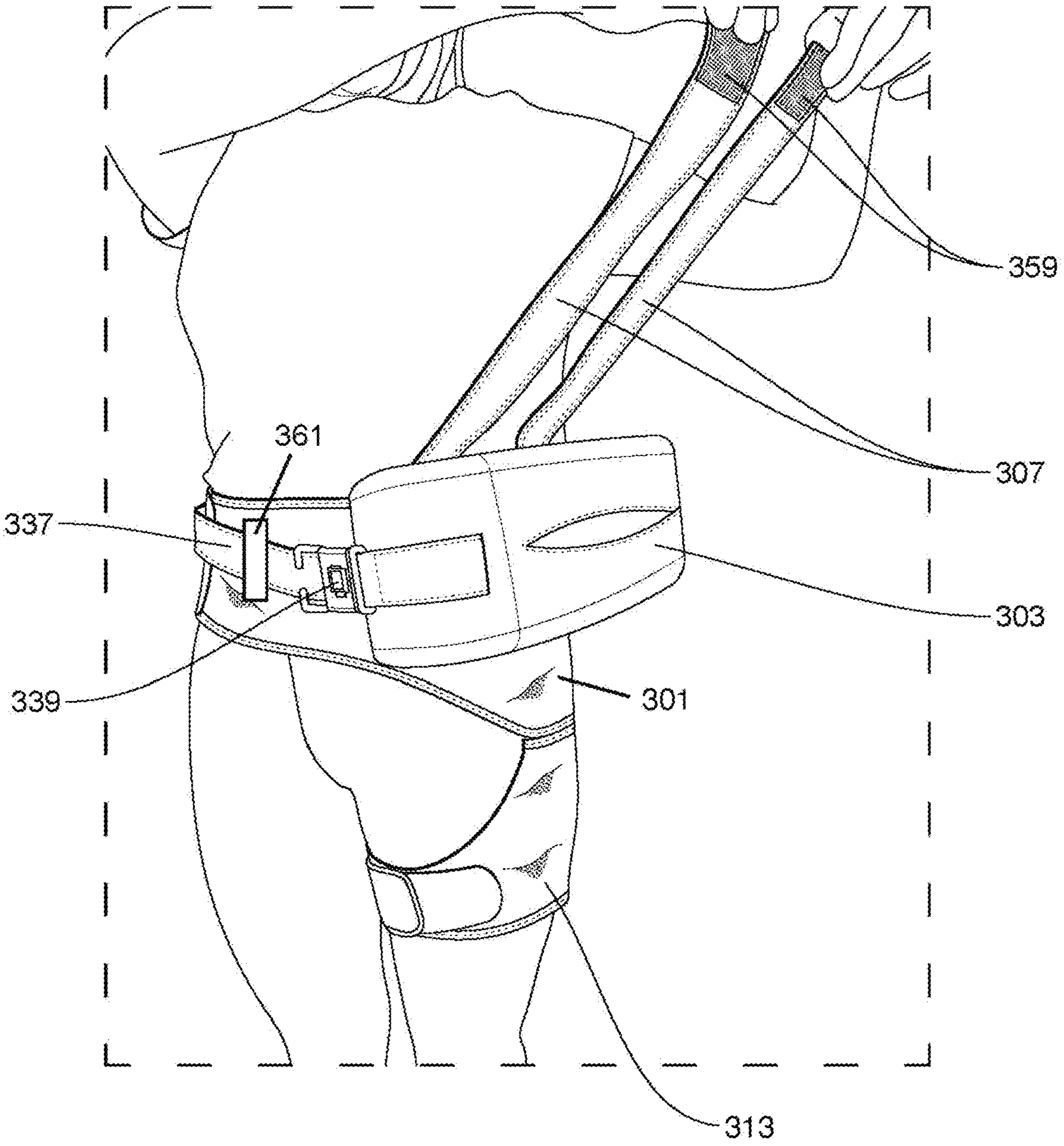
FIG. 25 illustrates a side view of a patient wearing an embodiment of a wrap member of the arm brace with two arm straps and an arm support member coupled to the wrap member.

FIG. 25 illustrates the wrap member 301 with the waist wrap piece 311 wrapped around the waist and the thigh wrap piece 313 wrapped around the thigh of the patient. The arm support member 303 can be detachably coupled to the wrap member 301. The arm straps 307 are coupled to the top connection region of the wrap member 301 and the arm support member 303. The arm straps 307 can be thin elongated structures that can be made of a flexible fabric material. A fastener 359 can be attached to the ends of the arm straps 307. The arm sleeve member can be placed against an outer side or top surface of the arm support member 303 and the arm straps 307 can wrap around the arm sleeve member. The fasteners 359 can be attached to the arm support member 303 to secure the arm sleeve member to the arm support member 303.

Figure 18:
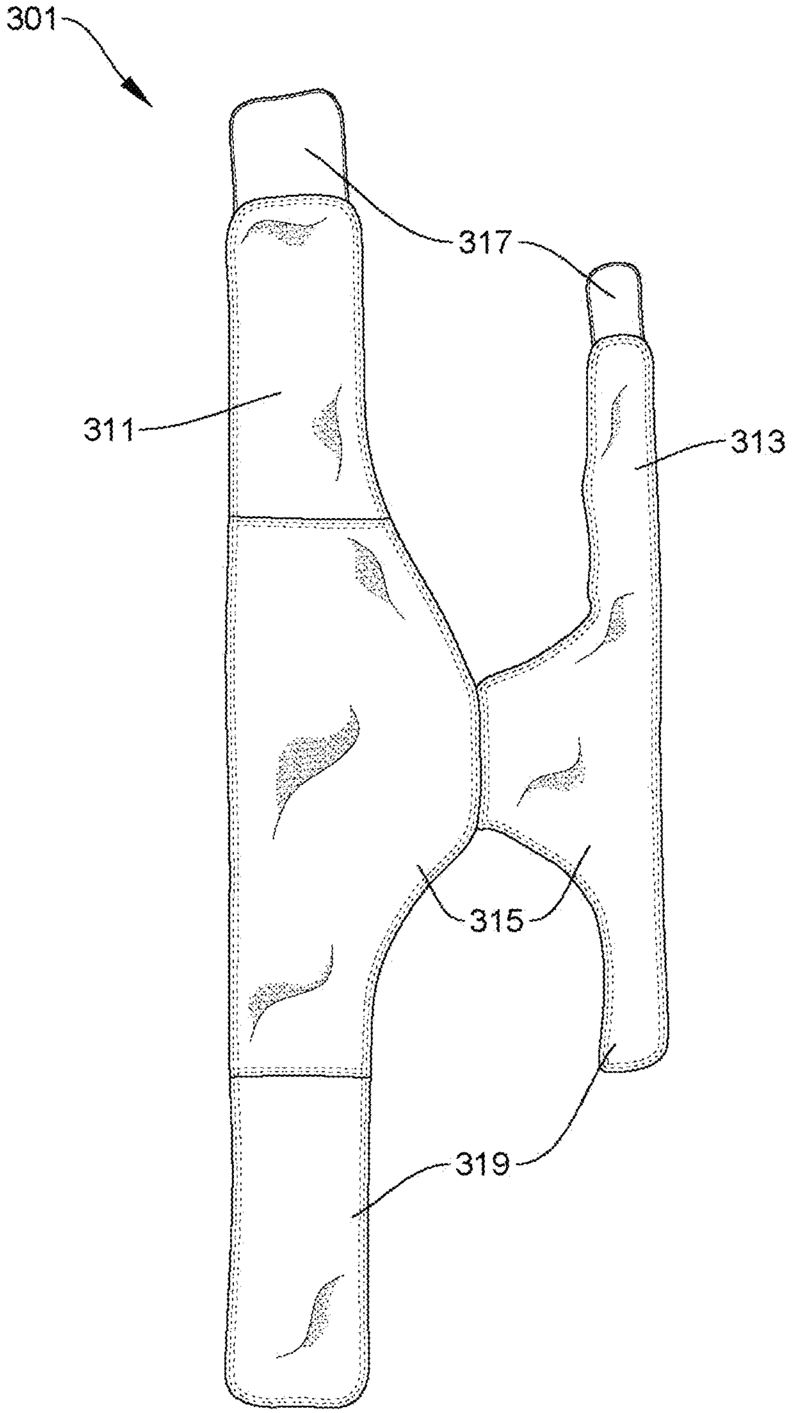
FIG. 18 illustrates a flat view of an embodiment of a wrap member of the arm brace.

FIG. 18 illustrates a top view of an embodiment of a wrap member of the arm brace. The wrap member 301 can have a waist wrap portion 311 adapted to wrap around the waist of a patient and a thigh wrap portion 313 adapted to wrap around the thigh of the patient. In some embodiments, the wrap member 301 can have a connection portion 315 that is between the waist wrap portion 311 and the thigh wrap portion 313. The connection portion 315 can connect the waist wrap portion 311 to the thigh wrap portion 313 forming a larger one piece structure. Both the waist wrap portion 311 and the thigh wrap portion 313 can have a first fastening member 317 at a first end and a second fastening member at a second end. The first fastening member 317 can be secured to the second fastening member 319 so that the wrap member 301 can be secured to the patient as shown in FIGS. 19 and 20. As discussed, the thigh wrap portion 313 secured to the thigh of the patient can cause the waist wrap portion 311 to remain stationary against the waist preventing rotation of the wrap member 301 and the arm support around the waist. In some embodiments, the first fastening member 317 can be a hook surface and the second fastening member 319 can be a loop surface. The wrap member 301 can be made of an elastic material, for example, neoprene or an inelastic material. In FIG. 18, the waist wrap portion is adapted to wrap around a waist of a user, the waist wrap portion having a first elongated waist strap and a second elongated waist strap that are illustrated as being roughly equal in length but in other embodiments the first elongated waist strap and a second elongated waist strap can have different lengths. The thigh wrap portion can have a first elongated thigh strap and a second elongated thigh strap that are illustrated as being roughly equal in length but in other embodiments the first elongated thigh strap and the second elongated thigh strap can have different lengths. The first fasteners 317 and second fasteners 319 can be hook and loop fasteners that can be pressed together to couple the first fasteners 317 to the second fasteners 319.

Figure 22:
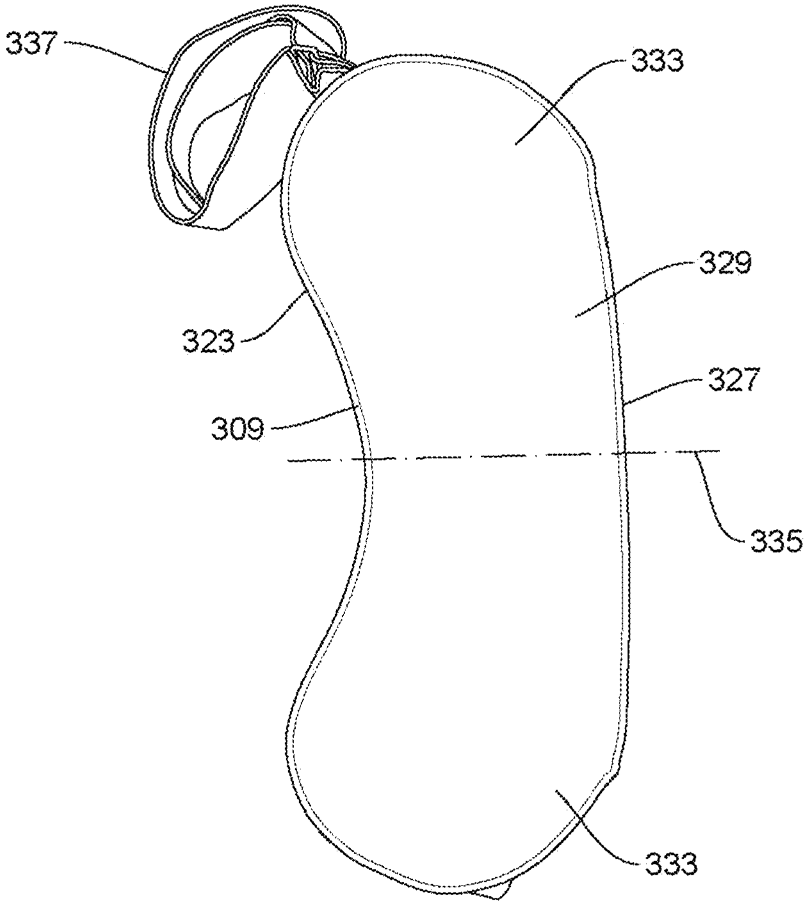
FIG. 22 illustrates a top view of an embodiment of an arm support member of the arm brace.

FIG. 22 illustrates a top view of an embodiment of an arm support member 303 of the arm brace. The arm support member 303 can have an inner concave side wall 309, an outer convex side wall 327, a planar top surface 329, a planar bottom surface 331 and two end walls 333 between the outer side wall 327 and the inner concave side wall 309. The side walls 309, 327, 333 can have curved or straight vertical surfaces. The inner concave side wall 309 can be a concave cylindrical surface that can roughly match the contour of a convex waist surface of a patient. The outer side wall 327 can be a straight or slightly convex cylindrical surface that the arm support member can comfortably rest against. Both the top surface 329 and the bottom surface can be planar, and the two end walls 333 can be convex curved cylindrical surfaces.

In some embodiments, the arm support member 303 can be symmetrical along an axis 335 perpendicular to the outer side wall 327 so that the arm support member 303 can be adaptable to support both a left forearm or a right forearm of a patient. The arm support member 303 can comprise a compressible foam structure that can be covered with a fabric material that can have a loop fastener surface.

Figure 21:
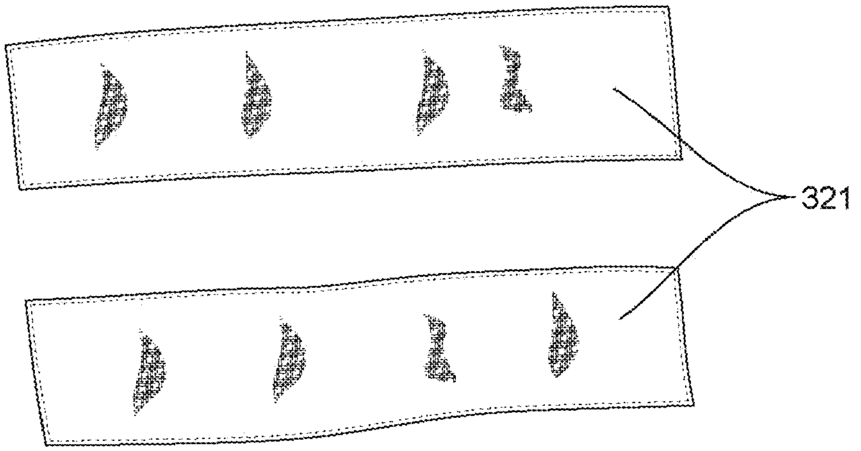
FIG. 21 illustrates a top flat view of an embodiment of a fastener for coupling a wrap member and an arm support member of the arm brace.

In some embodiments, a double-sided hook strip 321 as shown in FIG. 21 can be used to couple the arm support member 303 to the wrap member 301. The double-sided hook strip 321 can have two surfaces that can both have a hook fastener surface. The inner concave side wall 309 of the arm support member 303 having a loop surface can be detachably coupled to an outer surface of the wrap member 301 using one or more double-sided hook strips 321. The wrap member 301 can have a corresponding loop surface 325, and the arm support member 303 can have a corresponding loop surface 323. The double-sided hook strip 321 can engage with both the loop surface 323 of the arm support member 303 and the loop surface 325 of the wrap member 301.

Figure 24:
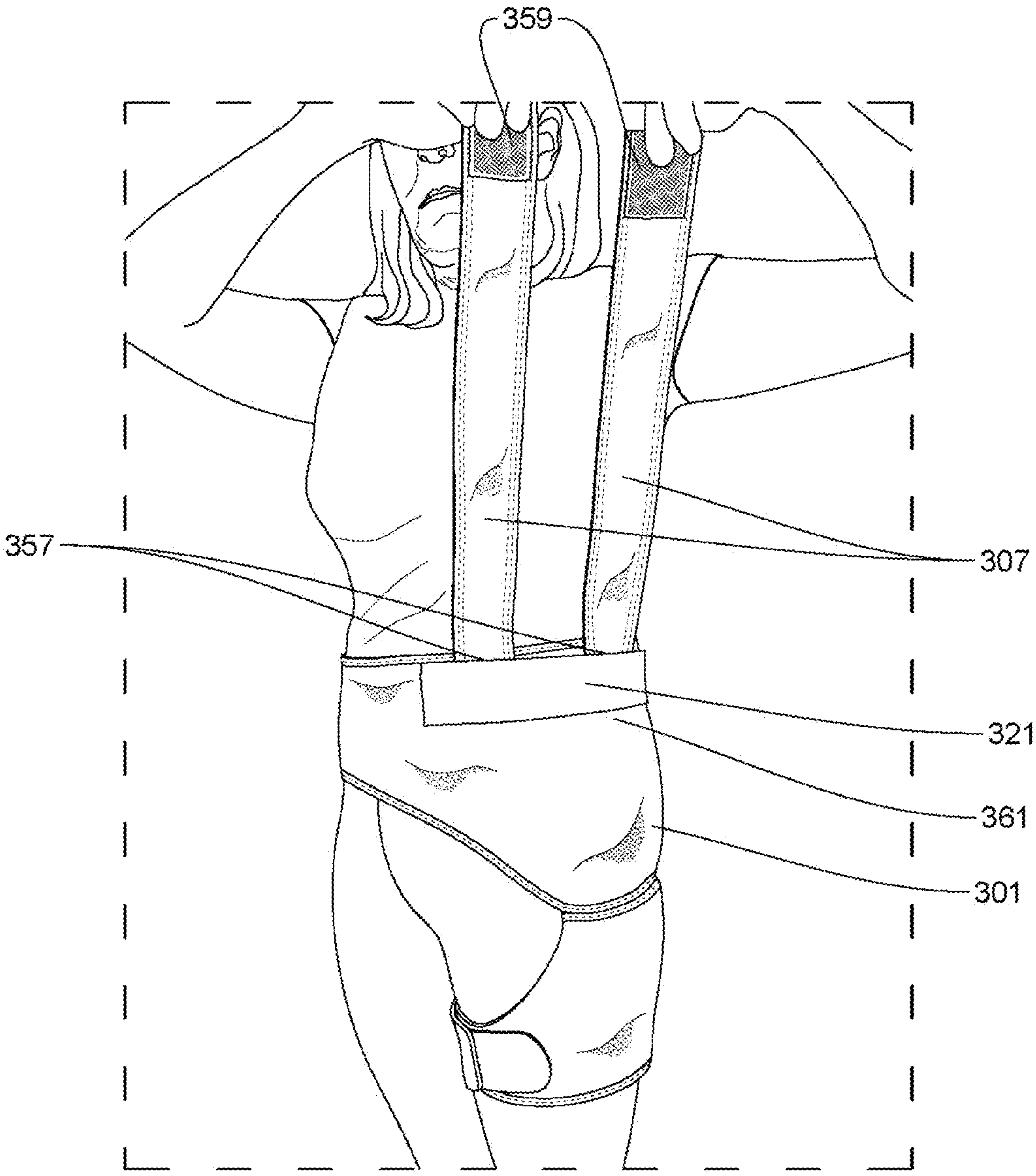
FIG. 24 illustrates a side view of a patient wearing an embodiment of a wrap member of the arm brace with two arm straps and a fastener for coupling the wrap member.

FIG. 24 shows that a double-sided hook strip 321 that has a hook fastener surface is secured to loop material at a top edge of the wrap member 301. The illustrated outer facing surface of the double-sided hook strip 321 is a hook fastener surface that can be ready for securing an inner facing loop surface of the arm support member 303. In some embodiments, the entire outer surface of the wrap member and the entire inner concave side wall can be a loop surface. Two double-sided hook strips can be used to couple the arm support member 303 to the wrap member 301 more securely.

In some embodiments, the arm support member can further have a fastening belt 337 with a buckle 339. The fastening belt 337 can wrap around the waist of a patient on an outer surface of the waist wrap portion 311 as shown in FIG. 25. The fastening belt 337 can supplement the hook and loop fastener mechanism to secure the arm support member 303 to the wrap member 301. The fastening belt 337 can be a flexible but inelastic fabric material. One end of the fastening belt 337 can be permanently secured to one end of the arm support member 303 and the opposite end of the fastening belt 337 can be releasably coupled to a buckle 339. The buckle 339 can allow the length and/or tension of the fastening belt 337 around the waist of the patient. The fastening belt 337 can be made of an inelastic material. The wrap member 301 can also have one or more belt loops 361 that can be positioned around the waist portion of the wrap member 301. The fastening belt 337 can pass through the one or more belt loops 361 to keep the fastening belt 337 over the waist portion of the wrap member 301.

As shown in FIG. 17, the arm sleeve member 305 can have two side walls 341, an end wall 343 at one end, a bottom 345, a top opening 347, and an end opening 349 at an opposite end. A forearm of a patient can be placed in the arm sleeve member 305 with the forearm between the two side walls 341. The forearm can rest at the bottom 345 of the arm sleeve member 305, and an elbow of the patient can be placed against the end wall 343 of the arm sleeve member 305. The hand of the patient can extend out the front end of the arm sleeve member 305 through the end opening 349 as shown in FIGS. 26-29.

As shown in FIG. 17, the arm brace 300 can have a fastener 351 to couple an outer side surface of the arm sleeve member 305 to the arm support member 303. In some embodiments, the fastener 351 can be a hook strip surface provided on an outer side wall 341 of the arm sleeve member 305, and the arm support member 303 can have a corresponding loop surface 353. In some embodiments, the entire top surface 329 and the entire outer side wall 327 of the arm support member 303 can be the loop fastener surface. In some embodiments, the hook strip surface can be provided on both side walls 341 of the arm sleeve member 305 so that the arm sleeve member 305 can be adaptable to both left/right forearms of a patient. In some embodiments, a hook strip surface can also be placed on an outer surface of the bottom 345 of the arm sleeve member 305 so that the bottom of the arm sleeve member 305 can be secured to the top surface of the arm support member 303. In some embodiments, the fastener 351 can be a double-sided hook strip that can be placed against and between a loop surface 353 of the arm support member 303 and a loop surface of the arm sleeve member 305 to secure the arm support member 303 to the arm sleeve member 305.

Figure 26:
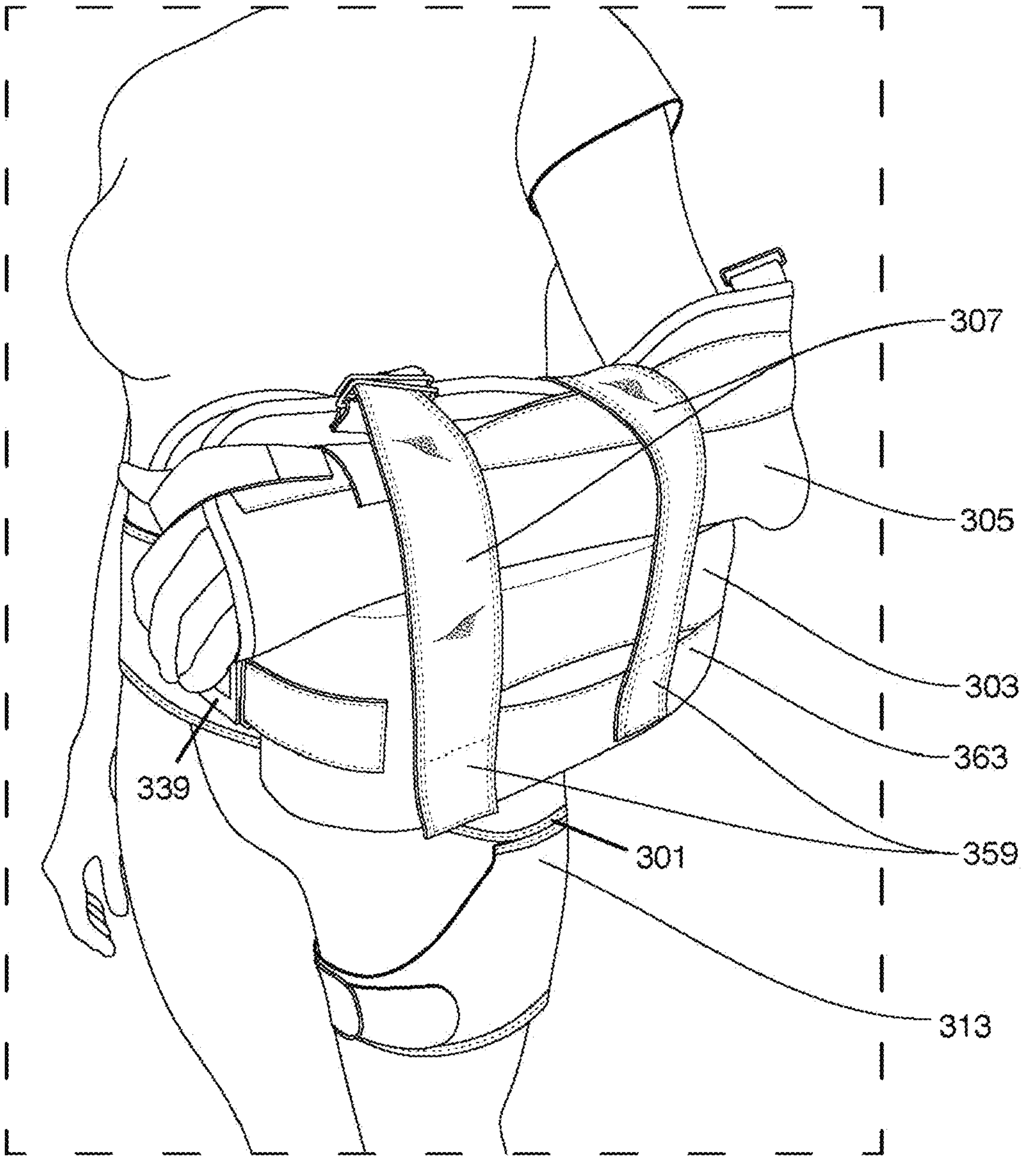
FIG. 26 illustrates a side view of a patient wearing an embodiment of the arm brace with a forearm of the patient on a top surface of an arm support member.
Figure 27:
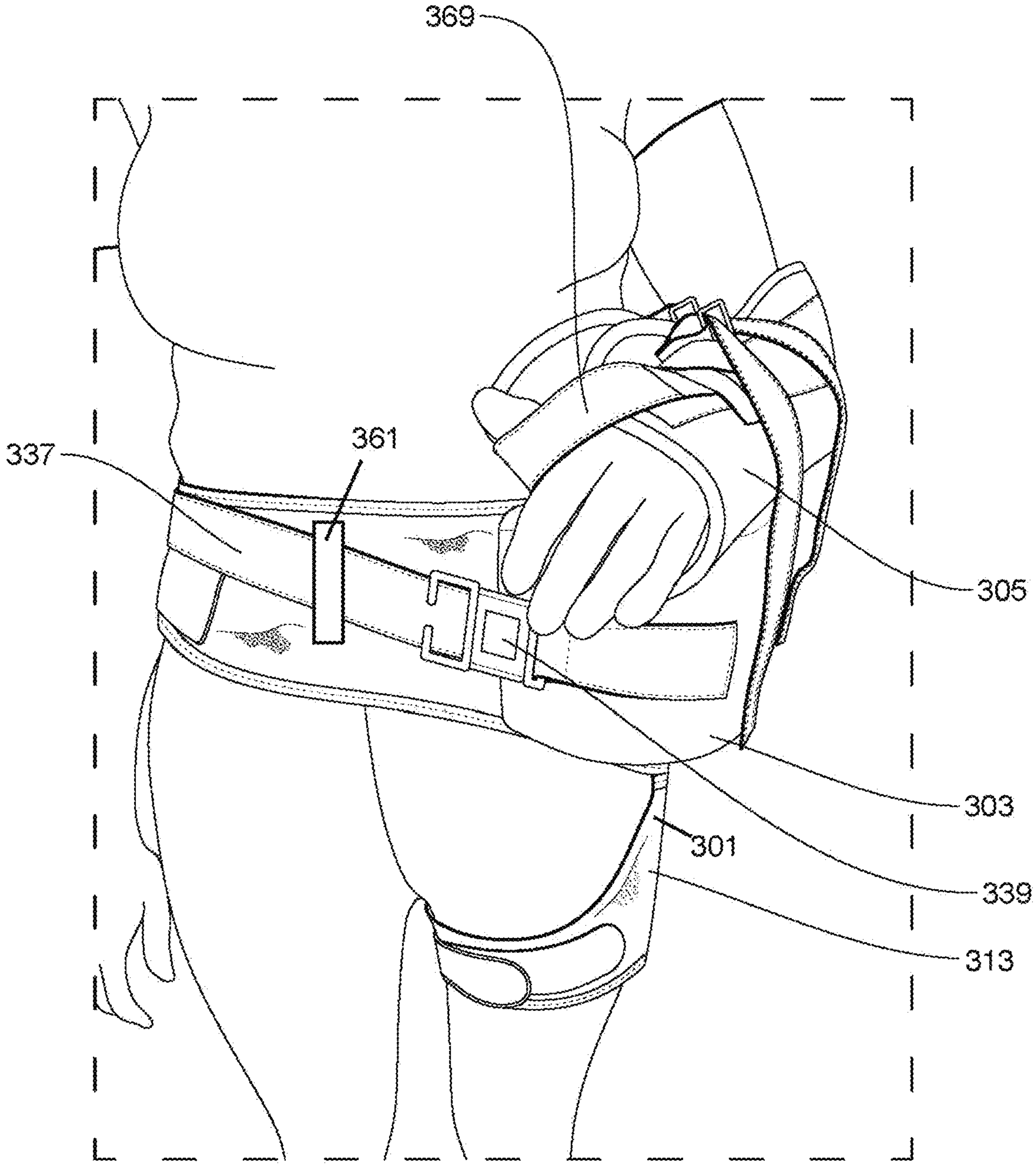
FIG. 27 illustrates a front view of a patient wearing an embodiment of the arm brace with a forearm of the patient on a top surface of an arm support member of the arm brace.
Figure 28:
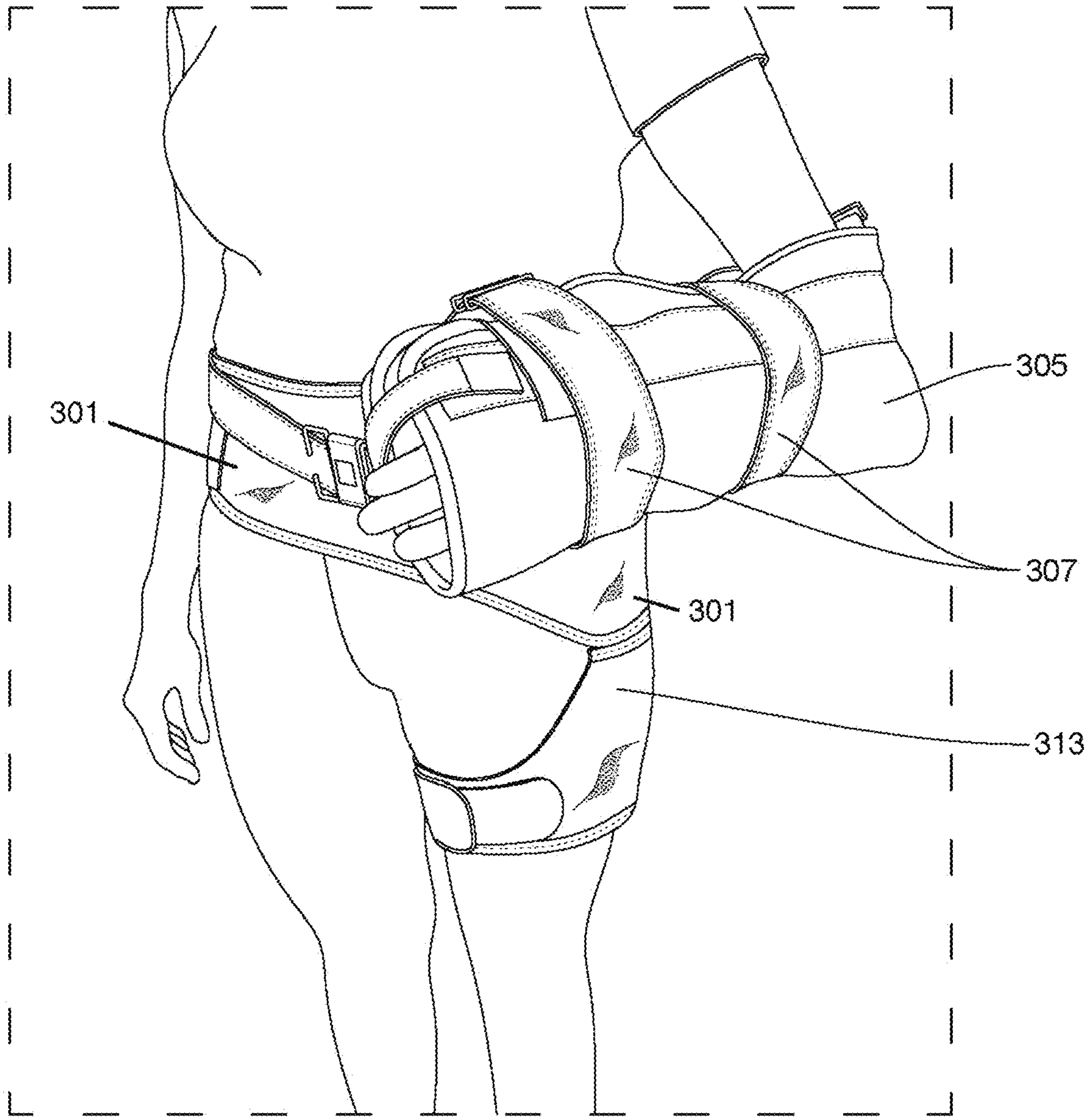
FIG. 28 illustrates a side view of a patient wearing an embodiment of the arm brace with a forearm of the patient against an outer side wall of an arm support member of the arm brace.
Figure 29:
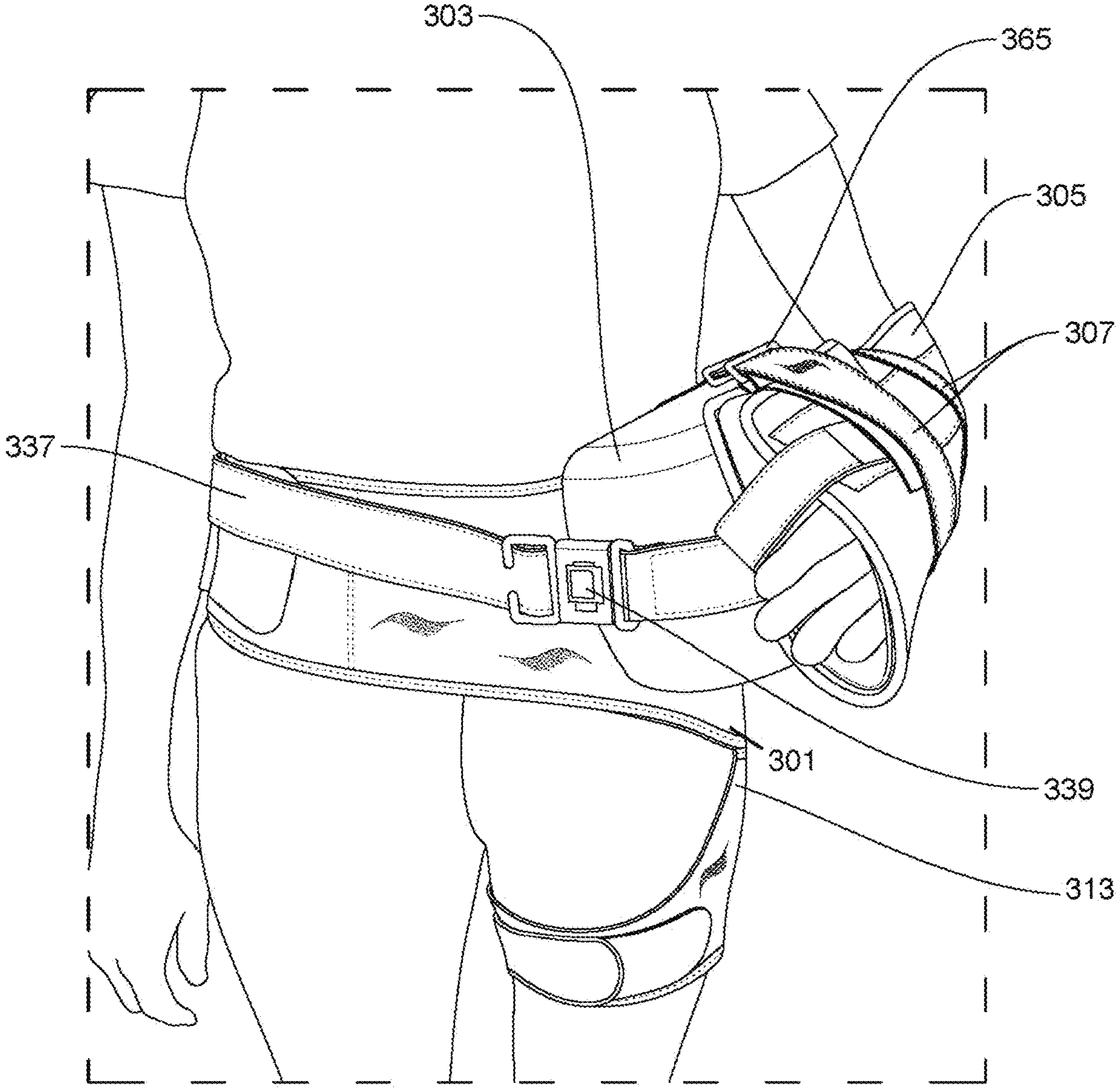
FIG. 29 illustrates a front view of a patient wearing an embodiment of the arm brace with a forearm of the patient against an outer side wall of an arm support member of the arm brace.

FIGS. 26 and 27 illustrate an embodiment of the arm sleeve member 305 placed on the top surface 329 of the arm support member 303. When the arm sleeve member 305 is placed on the top surface 329 of the support member 303 as shown in FIGS. 26 and 27, a hook strip surface on the outer surface of the bottom 345 of the arm sleeve member 305 can engage with a loop surface provided on the top surface 329 of the support member 303 to secure the arm sleeve member 305 to the arm support member 303. FIGS. 28 and 29 illustrate an embodiment of the arm sleeve member 305 placed against the outer side wall 327 of the arm support member 303. When the arm sleeve member 305 is placed against the outer side wall 327 of the support member 303 as shown in FIGS. 28 and 29, a hook strip surface on the side wall 341 of the arm sleeve member 305 can engage with a loop surface provided on the outer side wall 327 of the support member 303 to secure the arm sleeve member 305 to the arm support member 303. This flexible positioning of the forearm of a patient allows for more possible arm positions relative to the torso.

Figure 23:
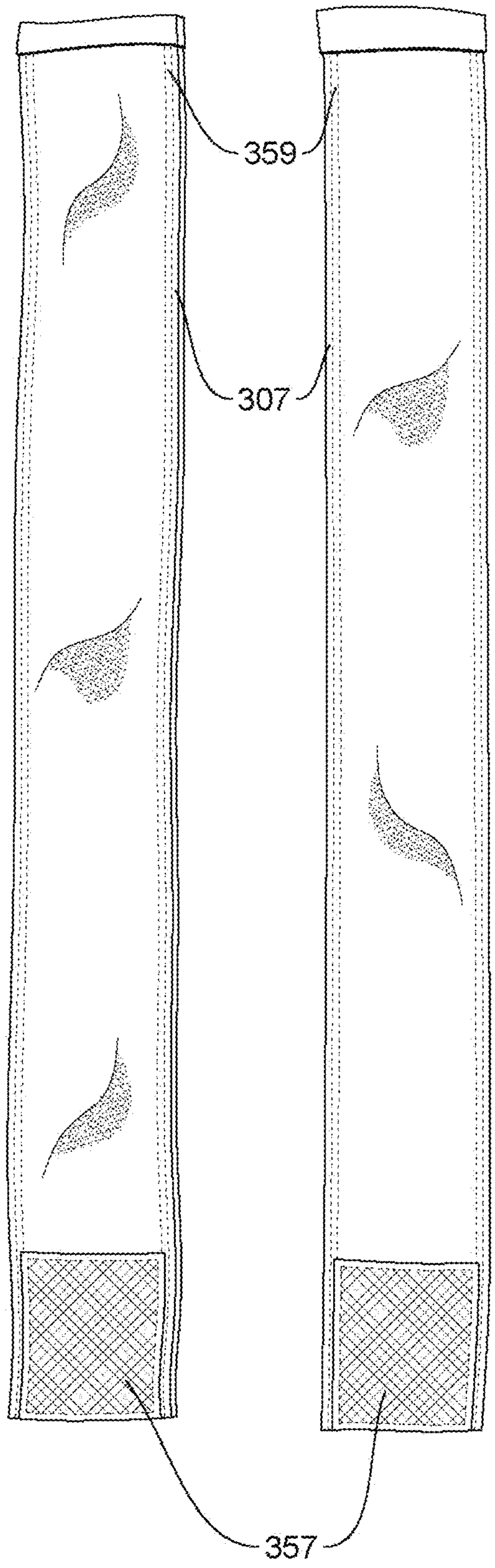
FIG. 23 illustrates a top flat view of an embodiment of an arm strap of the arm brace.

FIG. 23 illustrates a top view of an embodiment of two arm straps 307 that can be used to secure the arm sleeve member 305 to the arm support member 303 and the wrap member 301. The arm straps 307 can each have a hook fastener strip 357 provided at one end and a loop fastener strip 359 provided at the opposite end. In some other embodiments, both ends of the arm strap 307 can have loop fasteners.

FIGS. 24-26 illustrate a process for attaching the components of the arm support. FIG. 24 illustrates how the arm straps 307 can be coupled to the wrap member 301. The loop material ends 357 of the arm straps 307 can be fastened to the double sided hook fastener strip 321 that can secure the arm straps 307 to the wrap member 301. The hook material on the double sided hook fastener strip 321 can be fastened to the loop material on both the wrap member 301 and the arm straps 307.

FIG. 25 illustrates how the arm support 303 can be coupled to the wrap member 301. The loop fastener inner surface of the arm support 303 can be placed against the double sided hook fastener strip to secure the arm support 303 to the wrap member 301 with the arm straps 307 extending over the arm support 303. In the illustrated embodiment, the arm support 303 is also secured to the wrap member 301 with the fastening belt 337 that can be tightened around the waist with the locking member 339 that can be an adjustable buckle 339.

FIG. 26 illustrates how an arm in the sleeve member 305 can be secured to the top surface of the arm support 303. The sleeve member 305 can be placed on top of the arm support 303 and the arm strap 307 can wrap around the arm sleeve member 30 and over the outer surface of the arm support 303. The hook strips 359 at the ends of the arm straps 307 can be attached to the loop surfaces 363 on the outer surface of the arm support member 303 to secure the arm sleeve member 305 to the support arm member 303. The bottom outer surface of the sleeve member 305 can have a hook fastener surface that can be coupled to the loop material on the top of the arm support 303. The assembled arm support can provide support and stability for the forearm of the patient without any shoulder strap mechanisms.

In some embodiments, as shown in FIGS. 17 and 26-29, the arm sleeve member 305 can have strap loops 365 provided on top edges 367 of the side walls 341. The arm strap 307 can pass through the strap loops 365 to insure that the arm strap 307 is properly positioned over the front portion of the sleeve member 305 and can prevent the arm strap 307 from accidentally falling off of the sleeve member 305.

In some embodiments, as shown in FIGS. 26-29, the arm sleeve member 305 can have a thumb strap 369 adapted to connect both side walls 341 at the open end of the arm sleeve member 305. The thumb strap 369 can pass between a thumb and an index finger of a patient between the side walls 341 of the arm sleeve member 305. The thumb strap 369 can secure the front portion of the arm sleeve member 305 around the hand and provide support for the thumb of the patient. The thumb strap 369 can also limit the movement of a forearm of the patient relative to the arm sleeve member 305. In some embodiments, at each end of the end strap 369, there can be a hook strip surface that can engage with a loop surface on an outer front portion of the arm sleeve member 305.

FIGS. 25-29 illustrate the setup and use of the arm support with a left forearm. As discussed, the same arm support can be used to support either a left or a right forearm. When a right forearm of a patient needs to be immobilized, the wrap member 301 is attached to the patient with the waist wrap portion 311 wrapping around the waist of the patient and the thigh wrap portion 313 wrapping around the right thigh of the patient. The waist wrap portion 311 can be tightened around the waist and fasteners at front end portions of the waist wrap portion 311 can be secured to each other. Similarly, the thigh wrap portion 313, can be around the thigh and the ends of the thigh wrap portion 313 can be secured to each other. The wrap member 301 can be made of an elastic and/or an inelastic material that can be adaptable to patients with different waist and thigh sizes. In an embodiment, the waist wrap portion 311 can be made of an inelastic material and the thigh wrap portion 313 can be made of an elastic material. The arm straps 307 and the double-sided hook strip can then be coupled to the wrap member 301 by the hook and loop fasteners described above.

The inner concave surface 309 of the arm support member 303 can be attached to the wrap member 301 by the right hip of the patient. as described above. The right forearm can then be placed into the arm sleeve member 305 and the arm sleeve member 305 can be placed either on the top surface 329 or against the outer side wall 327 of the arm support member 303 as described above. The arm strap 307 can pass the strap loops 365 on the arm sleeve member 305. The arm straps 307 can wrap around the arm sleeve member 305 with the hook strips 359 being attached to the arm support member 303. The arm straps 307 can provide extra immobilization of the right forearm of the patient.

FIGS. 30-40 illustrate components and assemblies of another embodiment of an arm support apparatus. More specifically, FIGS. 30-38 illustrate a sequence of steps for assembling the arm brace with the arm sleeve member 305 coupled to an outer side surface of an arm support member 303. In other embodiments, the arm sleeve member 305 can be coupled to the top surface of an arm support member 303 as illustrated in and described with reference to FIGS. 39-42.

Figure 30:
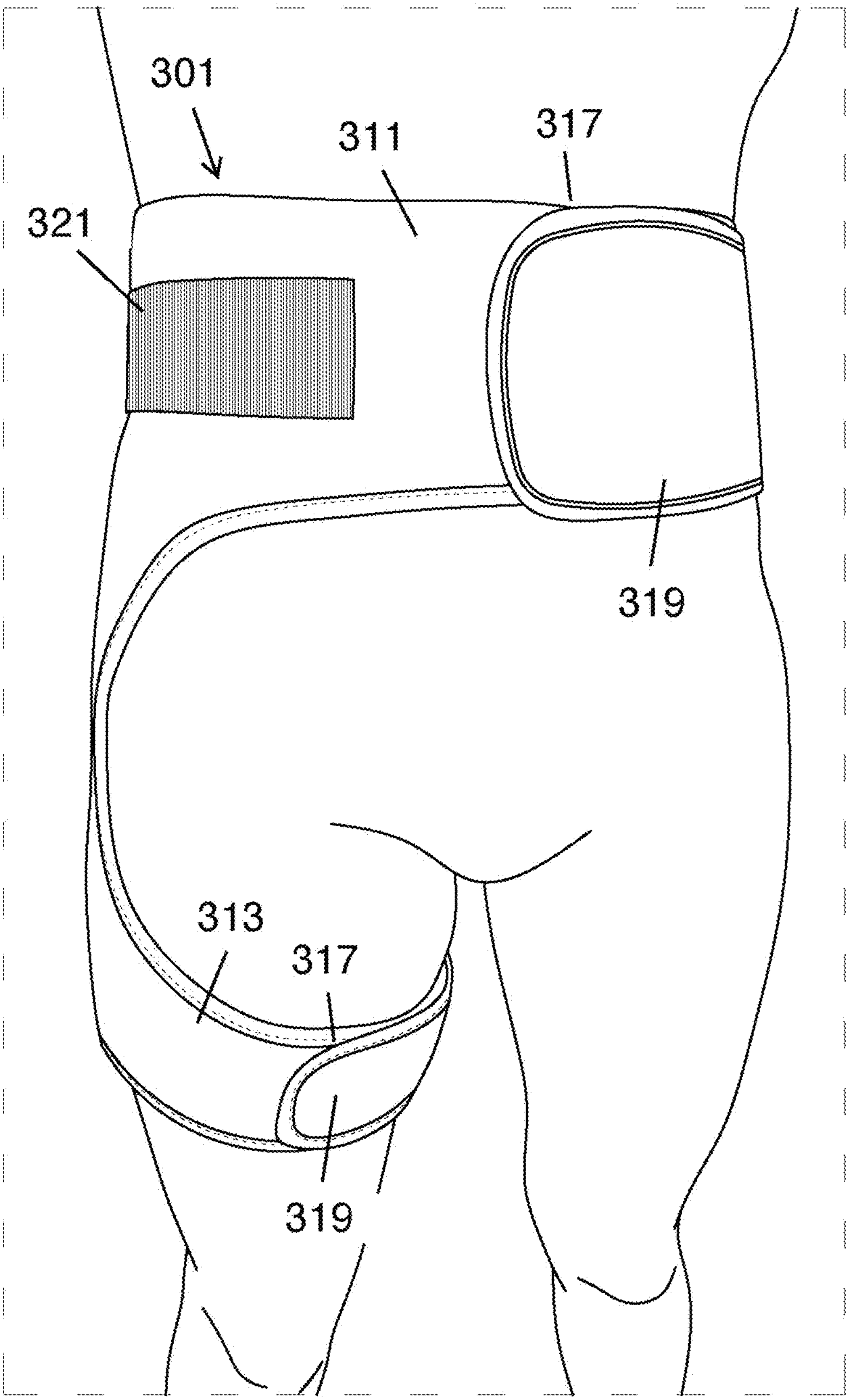
FIG. 30 illustrates a front perspective view of a patient wearing an embodiment of a wrap member of the arm brace.

The wrap member 301 is first placed on the patient. FIG. 30 illustrates a front perspective view of a patient wearing an embodiment of a wrap member 301 of the arm brace. The wrap member 301 can have a waist wrap piece 311 that wraps around the waist and a thigh wrap piece 313 that wraps around the thigh of a patient. The waist wrap piece 311 can be coupled to the thigh wrap piece 313. When the thigh wrap piece 313 is secured around the thigh, it can prevent the waist wrap piece 311 from sliding around the waist of the user that can provide a more stable arm support member 303 position.

Both the waist wrap portion 311 and the thigh wrap portion 313 can have a first fastening member 317 at a first end and a second fastening member at a second end. The first fastening member 317 can be secured to the second fastening member 319 so that the wrap member 301 can be secured to the patient. As discussed, the thigh wrap portion 313 secured to the thigh of the patient can cause the waist wrap portion 311 to remain stationary against the waist preventing rotation of the wrap member 301 and the arm support around the waist. In some embodiments, the first fastening member 317 can be a hook surface and the second fastening member 319 can be a loop surface. The wrap member 301 can be made of an elastic material, for example, neoprene or an inelastic material.

Figure 31:
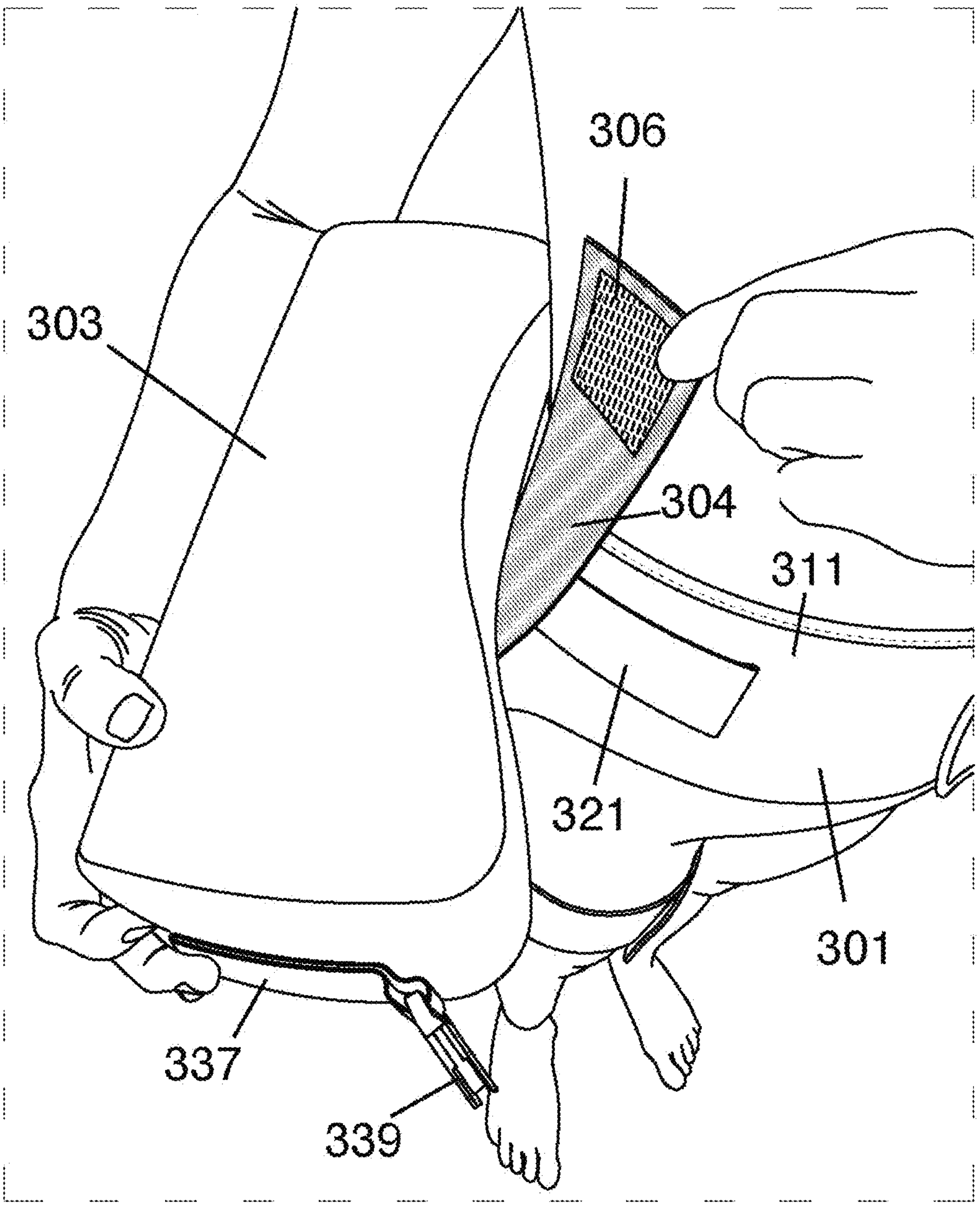
FIG. 31 illustrates a top perspective view of a patient wearing an embodiment of a wrap member of the arm brace with an arm support strap and an arm support member coupled to the wrap member.

The arm support member 303 is then coupled to the wrap member 301. FIG. 31 illustrates a top front perspective view of a patient wearing an embodiment of a wrap member 301 and an arm support member 303 being coupled to the wrap member 301. In some embodiments, a double-sided hook strip 321 can be used to couple the arm support member 303 to the wrap member 301. The double-sided hook strip 321 can have two surfaces that can both have a hook fastener surface. The inner concave side wall 309 of the arm support member 303 having a loop surface can be detachably coupled to an outer surface of the wrap member 301 using one or more double-sided hook strips 321. The wrap member 301 can have a corresponding loop surface 325, and the arm support member 303 can have a corresponding loop surface 323. The double-sided hook strip 321 can engage with both the loop surface 323 of the arm support member 303 and the loop surface 325 of the wrap member 301. In other embodiments, the hook strip 321 can be single sided with an inner surface permanently attached to the outer surface of the wrap member 301 and a hook surface facing outward from the wrap member 301.

Elongated strap 304 can be coupled to an outer surface of the wrap member 301 and extend upward. A fastener 306 such as a hook material surface can be on the end of the elongated strap 304. The elongated strap 304 can wrap over the top surface of the arm support member 303 and the fastener 306 can be coupled to the loop fabric on the top surface of the arm support member 303. The elongated strap 304 can secure the middle portion of the arm support member 303 to the waist portion of the wrap member 301. In other embodiments, the components described with reference to FIG. 24 can be used to secure the arm support member 303 to the waist portion of the wrap member 301.

Figure 32:
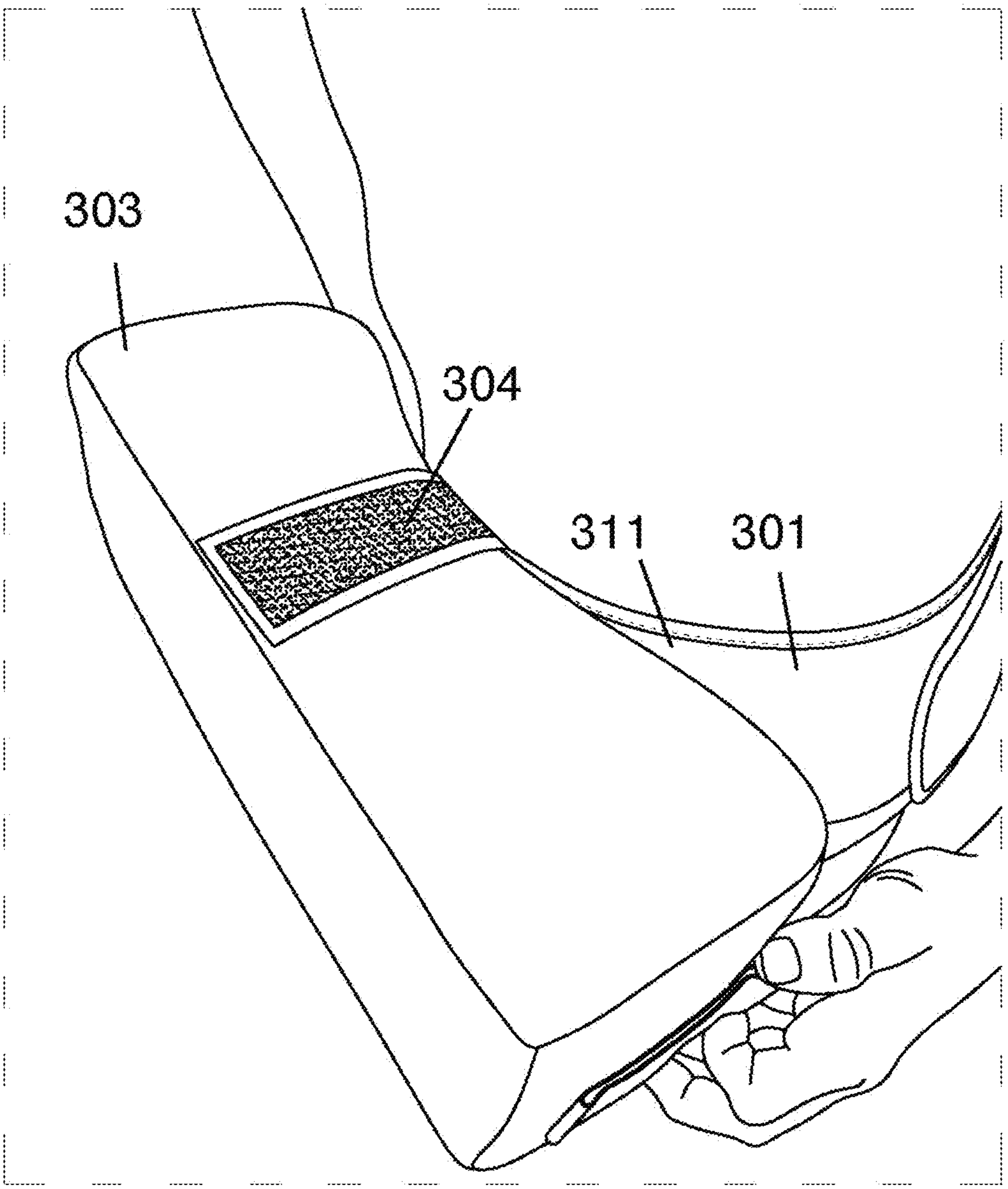
FIG. 32 illustrates a top perspective view of a patient wearing an embodiment of a wrap member of the arm brace with an arm support strap coupled to an arm support member coupled and the wrap member.

FIG. 32 illustrates a top perspective view of a patient wearing an embodiment of a wrap member of the arm brace with an arm support strap coupled to an arm support member coupled and the wrap member. In other embodiments, the elongated strap 304 can be attached between the patient and the inner surface of the waist portion 311 of the wrap member 301. The upper surface and upper inner edge of the arm support member 303 can be aligned with the upper edge of the wrap member 301. This configuration may provide a more secure hold of the arm support member 303 to the wrap member 301.

Figure 39:
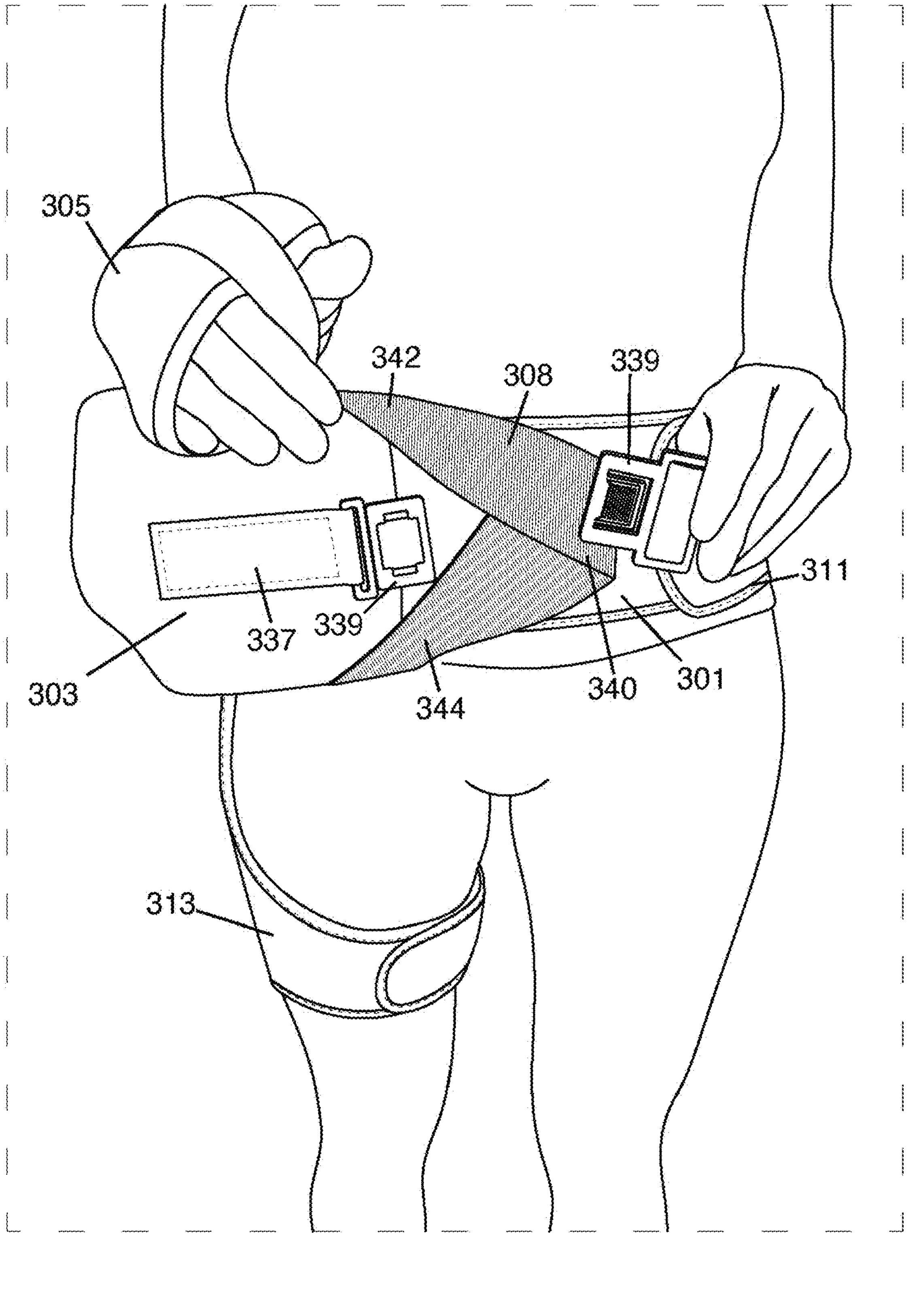
FIG. 39 illustrates a front view of a patient wearing an embodiment of the arm brace with a forearm of the patient on an upper side surface of an arm support member and a front V strap coupled to the arm support and the wrap member and a belt over the front V strap.

FIG. 39 illustrates a coupling side surface and FIG. 39 illustrates an outer side surface of an embodiment of a V strap 308. In the illustrated embodiment, the V strap 308 has a first elongated section 342 and a second elongated section 344 that meet at a center portion 340. Fasteners 346 such as hook pieces or loop pieces can be attached to the center 340 and the ends of the first elongated section 342 and the second elongated section 344. In other embodiments the fasteners 346 can be any other suitable releasable connection mechanism such as buttons, snap couplings, screws/bolts, adhesives, etc.

The V strap 308 can be made of a flat flexible inelastic material such as fabric webbing that can be folded at the center portion 340. In some embodiments, the center portion 340 can be sewn to hold the V strap 308 in a folded configuration. In other embodiments the V strap 308 can be made of other flexible inelastic materials such as plastic, rubber, composites such as laminated fibers, or other suitable materials. The V strap 308 can be formed in various different manners including stamping from sheet stock of materials, 3D printing, laminating, molding, etc.

The fasteners 346 can be areas of hook and/or loop material that can be securely attached to the center portion 340 and the ends of the first elongated section 342 and the second elongated section 344. The fasteners 346 can be attached to the V straps 308 in various different ways including sewing, adhesively bonding, heat fusing, stapling, or other suitable connection methods.

The first elongated section 342 and the second elongated section 344 can form an angle between about 20 and 80 degrees. The first elongated section 342 and the second elongated section 344 can be about ½ to 4 inches wide. The first elongated section 342 and the second elongated section 344 can be between about 2 and 20 inches long.

The first elongated section 342 and the second elongated section 344 can be attached to the front end and back end of the arm support member 303 and then pulled in tension. The center portion 340 can then be connected to the wrap member 301. In some embodiments the fasteners can be hook material that can be securely coupled to the loop fabric on the outer surfaces of the arm support member 303 and the wrap member 301. This configuration can securely hold the arm support member 303 to the wrap member 301 so that the arm can be properly supported by the brace without any structures that extend above the elbow of the patient such as neck or shoulder straps.

Figure 33:
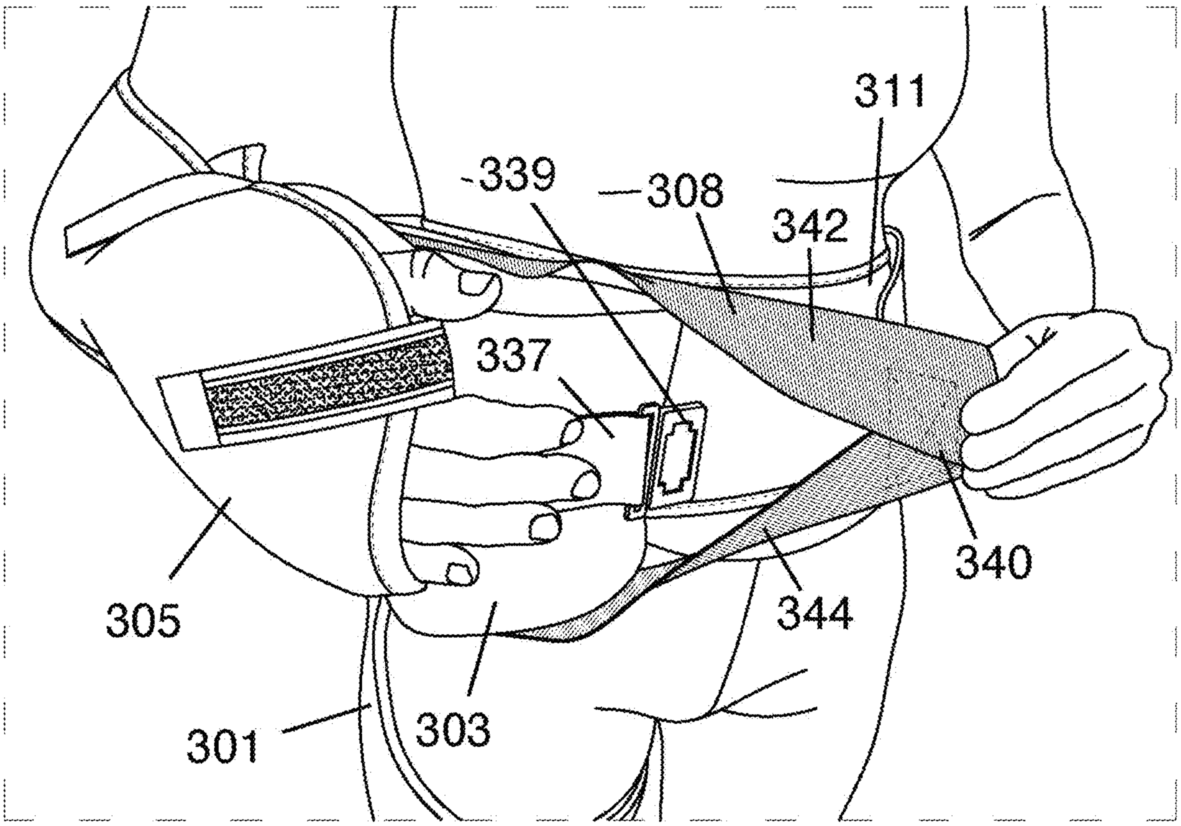
FIG. 33 illustrates a side view of a patient wearing an embodiment of the arm brace with a forearm of the patient on an outer side surface of an arm support member and a front V strap coupled to the arm support.

A front V strap 308 can be used to secure and support a front portion of the arm support member 303 to the wrap member 301. FIG. 33 illustrates a side view of a patient wearing an embodiment of the arm brace with a forearm of the patient in an arm sleeve member 305 that is attached to an outer side surface of an arm support member 303. A front V strap 308 can have a first elongated piece 342 that can be attached to an upper surface of the arm support member 303 and a second elongated piece 344 that can be attached to a lower surface of the arm support member 303. The ends of the first elongated piece 342 and the second elongated piece 344 can have fasteners such as loop or hook surfaces that can be attached to the arm support member 303. The center portion 340 can then be pulled in tension and attached to the waist portion of the wrap member 301. The center portion 340 of the V strap 308 can have a fastener such as loop or hook surfaces that can be attached to the waist portion 311 of the wrap member 301.

Figure 34:
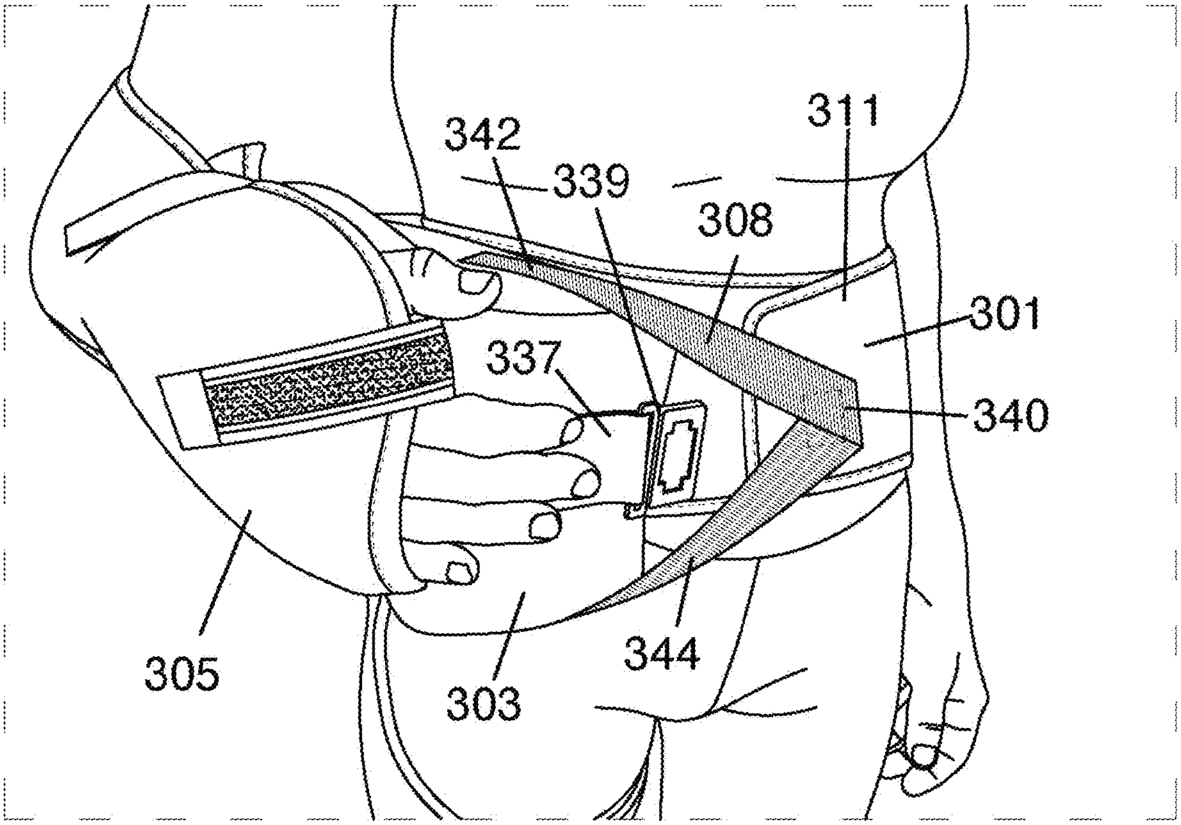
FIG. 34 illustrates a side view of a patient wearing an embodiment of the arm brace with a forearm of the patient on an outer side surface of an arm support member and a front V strap coupled to the arm support and the wrap member.
Figure 35:
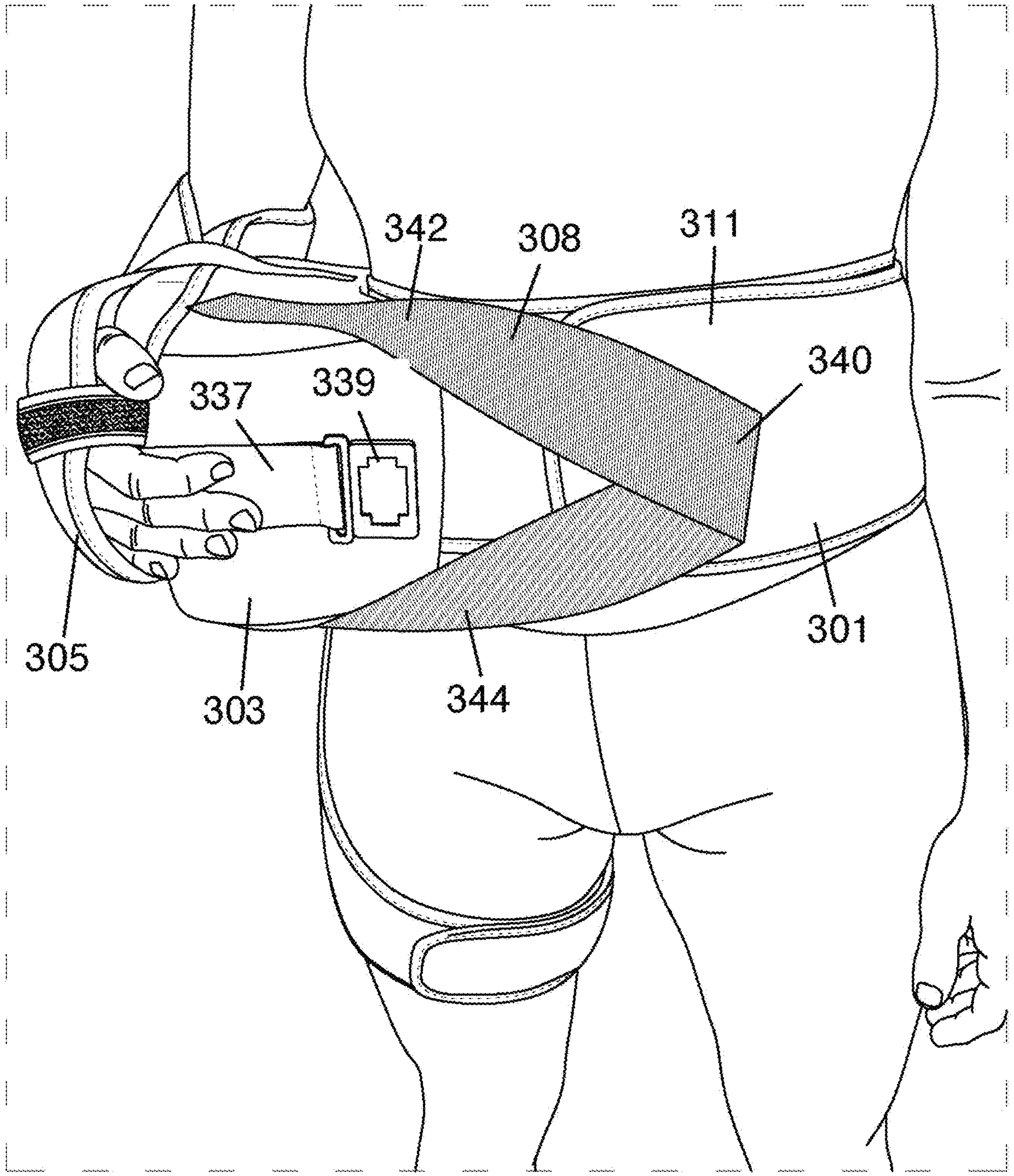
FIG. 35 illustrates a front view of a patient wearing an embodiment of the arm brace with a forearm of the patient on an outer side surface of an arm support member and a front V strap coupled to the arm support and the wrap member.

FIGS. 34 and 35 illustrate side front views of a patient wearing an embodiment of the arm brace with a forearm of the patient in an arm sleeve member 305 coupled to an outer side surface of an arm support member 303. The ends of the first elongated piece 342 and the second elongated piece 344 of the front V strap 308 are coupled to the upper and lower surfaces of the arm support member 303. The center portion 340 of the V strap 308 the front surface of the waist portion 311 of the wrap member 301. The V strap 308 provides support to the arm support member 303 to securely connect the arm support member 303 to the wrap member 301.

Figure 36:
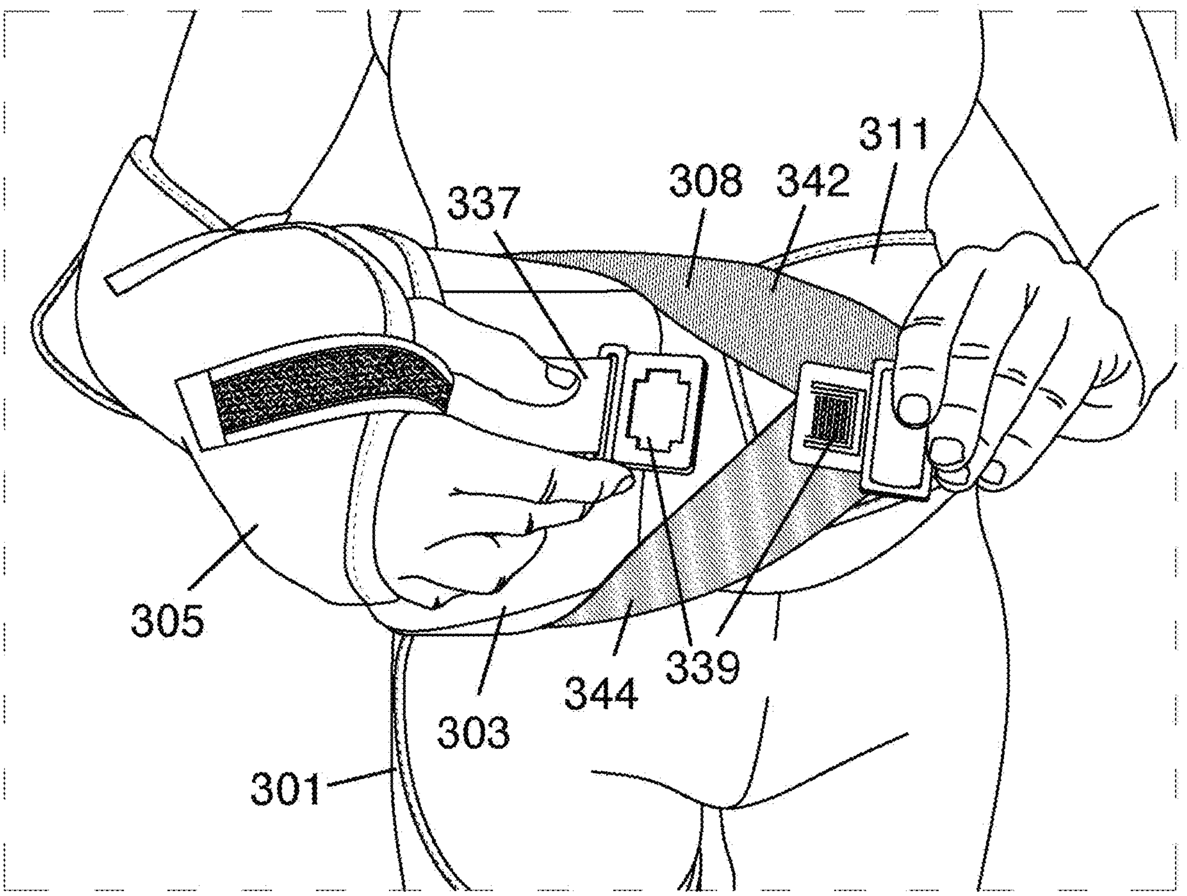
FIG. 36 illustrates a front view of a patient wearing an embodiment of the arm brace with a forearm of the patient on an outer side surface of an arm support member and a front V strap coupled to the arm support and the wrap member and a belt over the front V strap.

FIG. 36 illustrates a front view of a patient wearing an embodiment of the arm brace with a forearm of the patient in the arm sleeve member 305 coupled to the outer side surface of an arm support member 303. The front V strap 308 is coupled to the arm support member 303 and the center portion of the front V strap 308 is coupled is coupled to the waist portion 311 of the wrap member 301. The front surface of the wrap member and a fastening belt buckle are placed over the front V strap 308. A fastening belt 337 can wrap around the outer surface of the arm support member 303 and the waist portion 311 of the wrap member 301. The fastening belt 337 can be adjustable in length and can have releasable buckles 339 attached to the ends of the fastening belt 337. The fastening belt 337 can wrap around the waist of a patient on the outer surface of the waist wrap portion 311. The length of the fastening belt 337 can be adjusted so that the fastening belt 337 securely holds the arm support member 303 to the waist portion 311 of the wrap member 301 and the patient when the releasable buckles 339 are connected.

Figure 37:
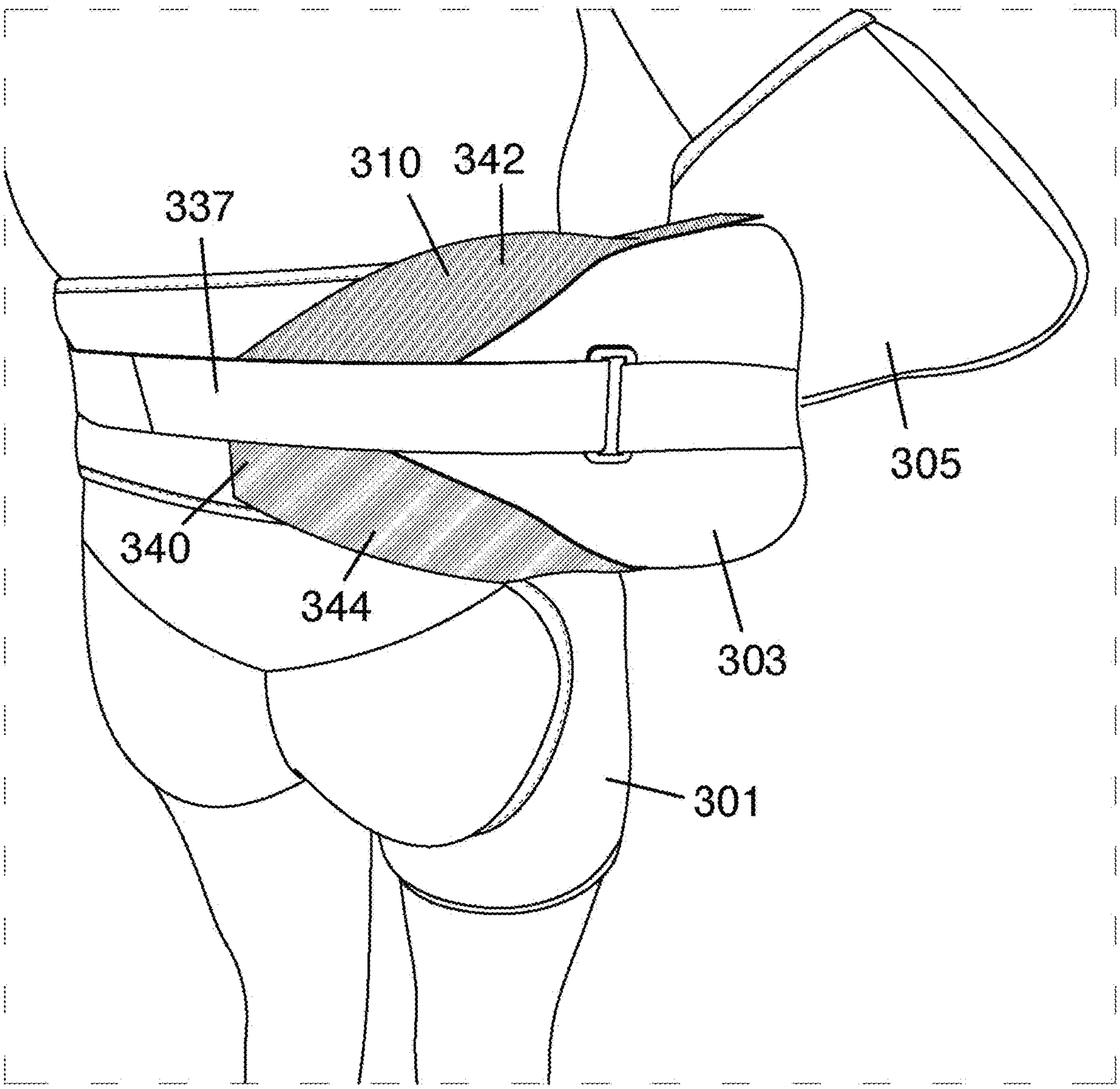
FIG. 37 illustrates a rear view of a patient wearing an embodiment of the arm brace with a forearm of the patient on an outer side surface of an arm support member and a rear V strap coupled to the arm support and the wrap member and a belt over the rear V strap.

FIG. 37 illustrates a rear view of a patient wearing an embodiment of the arm brace with a forearm of the patient in the arm sleeve member 305 coupled to the outer side surface of an arm support member 303 and a rear V strap 310 coupled to the rear portion of the arm support 303 and the rear outer surface of the wrap member 301. The rear V strap 310 can be identical to the front V strap 308. The ends of the first elongated piece 342 and the second elongated piece 344 of the rear V strap 310 are coupled to the upper and lower surfaces of the arm support member 303. The center portion 340 of the rear V strap 310 is attached to the rear surface of the waist portion 311 of the wrap member 301. The rear V strap 310 also provides support to the arm support member 303 to securely connect the arm support member 303 to the wrap member 301. The fastening belt 337 is placed over the center portion 340 of the rear V strap 310. The tension of the fastening belt 337 helps to secure the center portion 340 of the rear V strap 310 to the wrap member 301.

Figure 38:
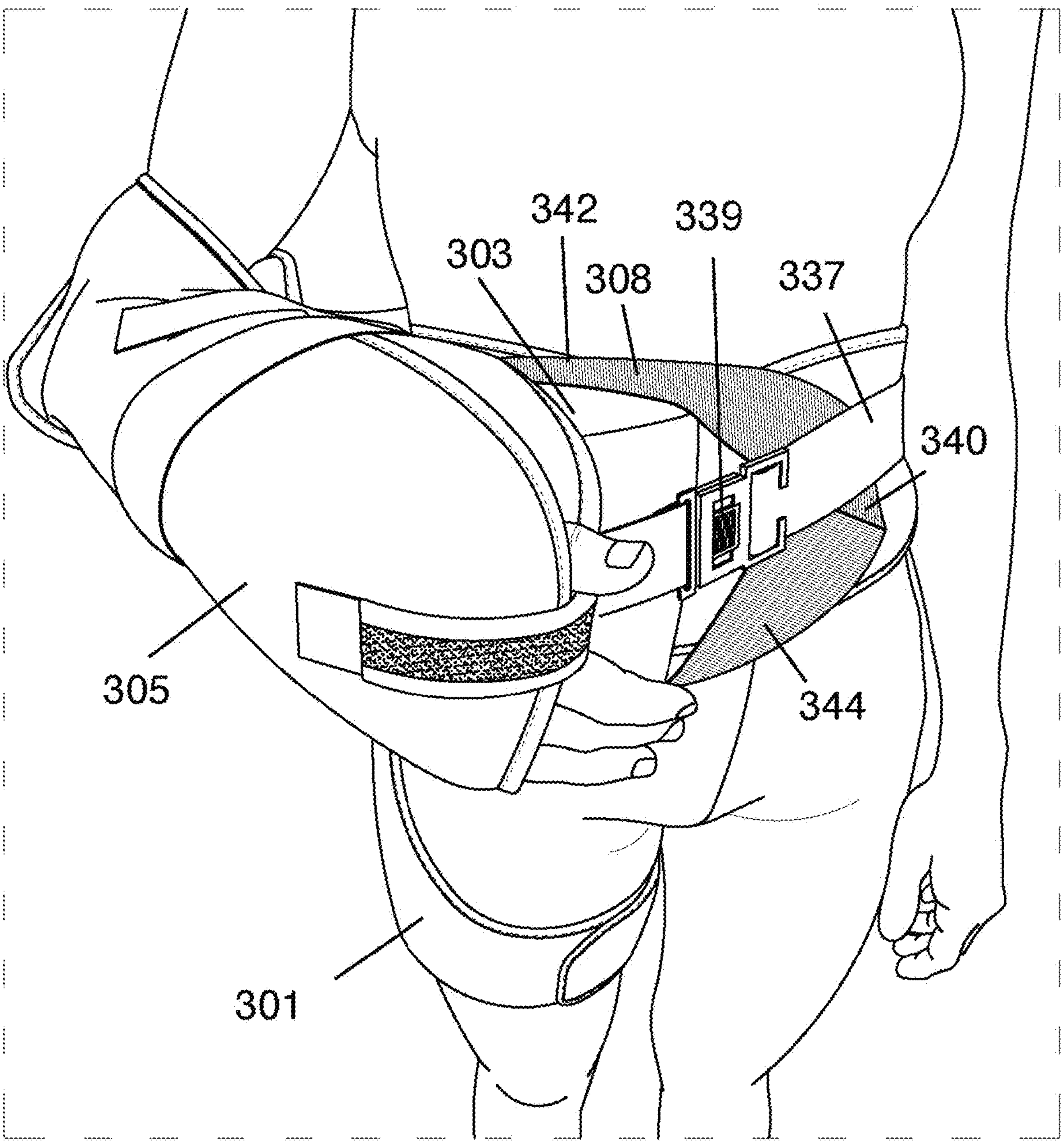
FIG. 38 illustrates a front view of a patient wearing an embodiment of the arm brace with a forearm of the patient on an outer side surface of an arm support member and a front V strap coupled to the arm support and the wrap member and a belt buckle over the front V strap.

FIG. 38 illustrates a front view of a patient wearing an embodiment of the arm brace with a forearm of the patient in the arm sleeve member 305 coupled to an outer side surface of an arm support member 303. The front V strap 308 is coupled to the arm support 303 and the front surface of the wrap member 301. The fastening belt 337 extends over the center portions 340 of the front V strap 308 and the rear V strap 310. The releasable buckles 339 at the ends of the fastening belt 337 are connected and the tension of the fastening belt 337 helps to secure the center portion 340 of the rear V strap 310 to the wrap member 301. The arm brace supports an injured arm during rehabilitation and does not require a shoulder strap, a neck strap for support and any other upper body supports.

FIG. 39 illustrates a front view of a patient wearing an embodiment of the arm brace with a forearm of the patient in the arm sleeve member 305 coupled to the upper side surface of an arm support member 303. The front V strap 308 is coupled to the arm support member 303 and the center portion of the front V strap 308 is coupled is coupled to the waist portion 311 of the wrap member 301. The front surface of the wrap member and a fastening belt buckle are placed over the front V strap 308. A fastening belt 337 can wrap around the outer surface of the arm support member 303 and the waist portion 311 of the wrap member 301. The fastening belt 337 can be adjustable in length and can have releasable buckles 339 attached to the ends of the fastening belt 337. The fastening belt 337 can wrap around the waist of a patient on the outer surface of the waist wrap portion 311. The length of the fastening belt 337 can be adjusted so that the fastening belt 337 securely holds the arm support member 303 to the waist portion 311 of the wrap member 301 and the patient when the releasable buckles 339 are connected.

Figure 40:
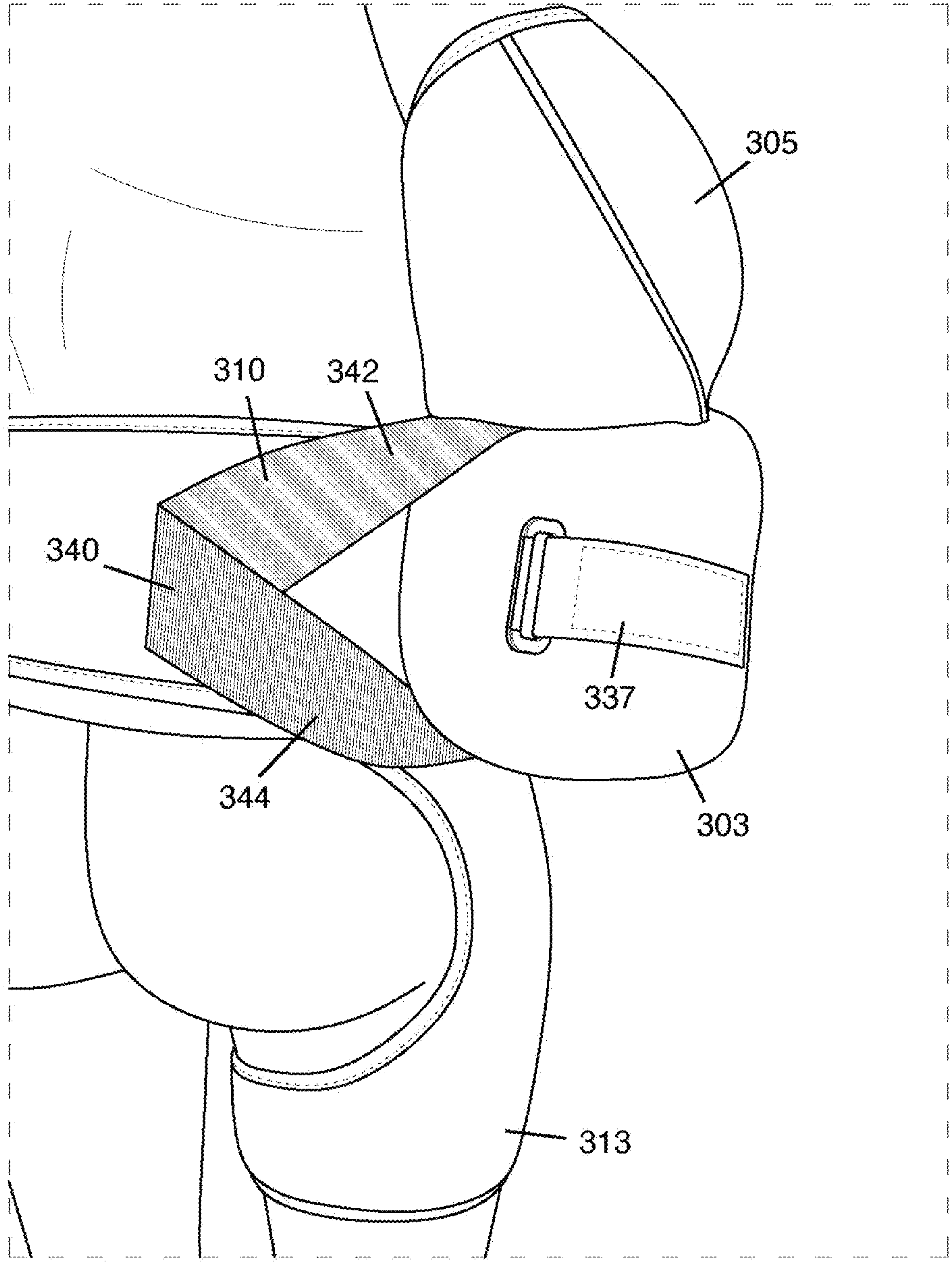
FIG. 40 illustrates a rear view of a patient wearing an embodiment of the arm brace with a forearm of the patient on an upper side surface of an arm support member and a rear V strap coupled to the arm support.
Figure 41:
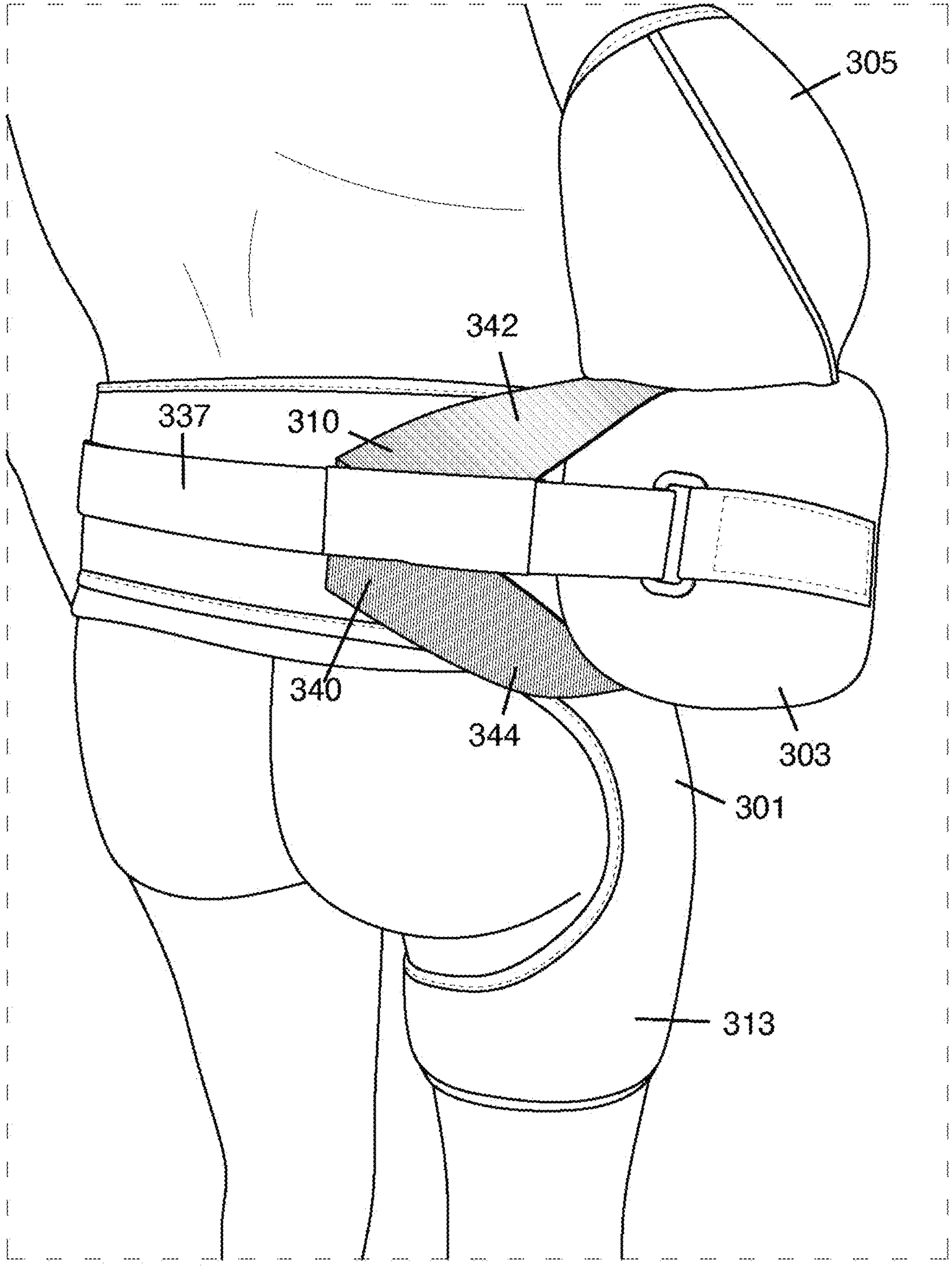
FIG. 41 illustrates a rear view of a patient wearing an embodiment of the arm brace with a forearm of the patient on an upper side surface of an arm support member and a rear V strap coupled to the arm support and the wrap member and a belt over the rear V strap.
Figure 42:
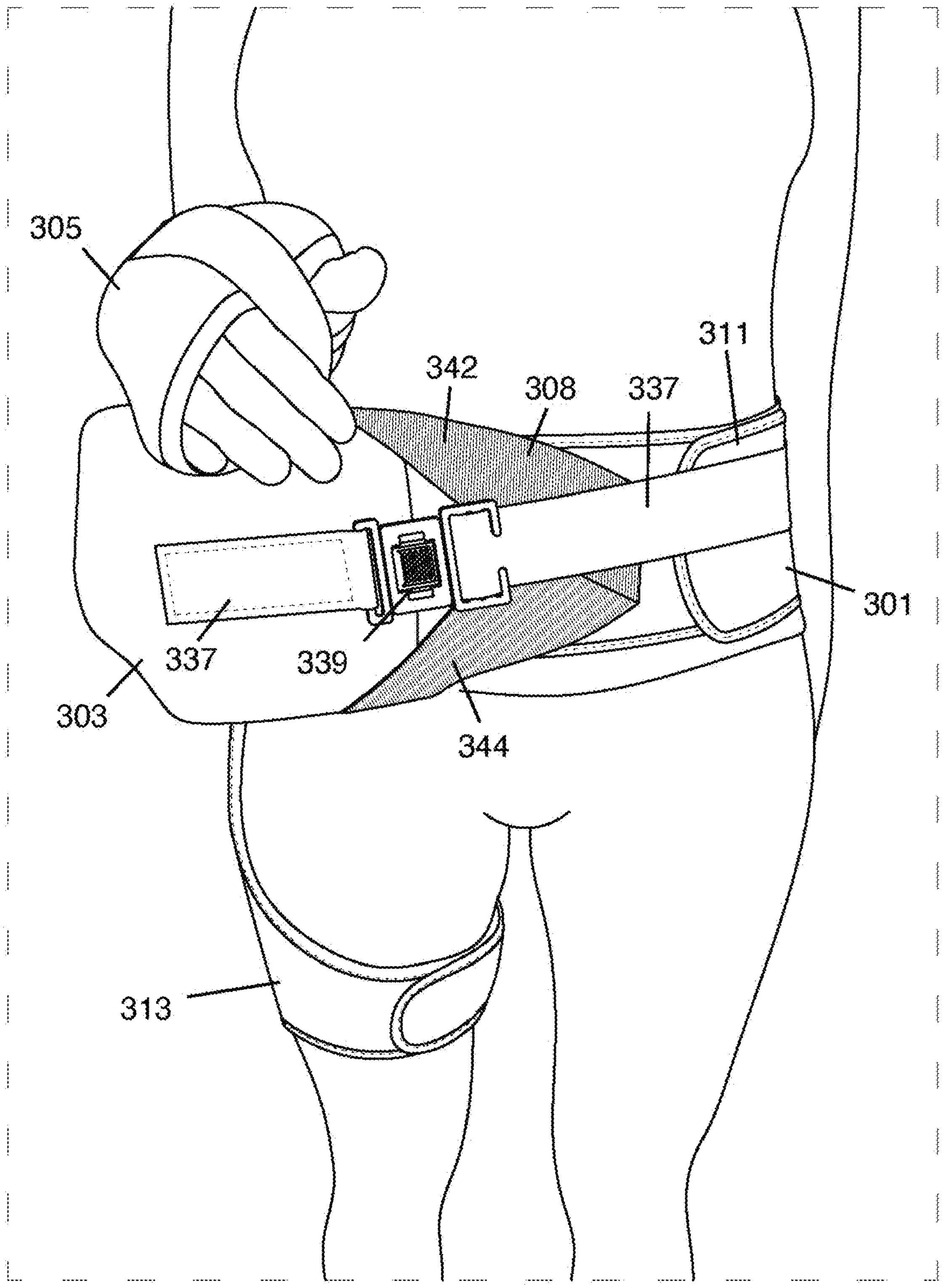
FIG. 42 illustrates a front view of a patient wearing an embodiment of the arm brace with a forearm of the patient on an upper side surface of an arm support member and a front V strap coupled to the arm support and the wrap member and a belt buckle over the front V strap.
Figure 43:
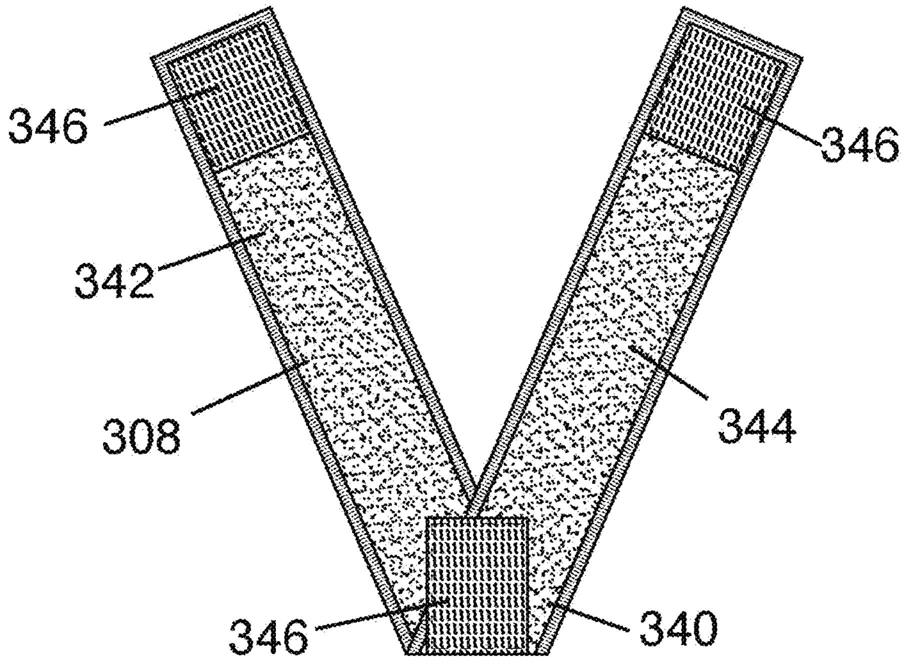
FIG. 43 illustrates a coupling surface of an embodiment of a V strap.
Figure 44:
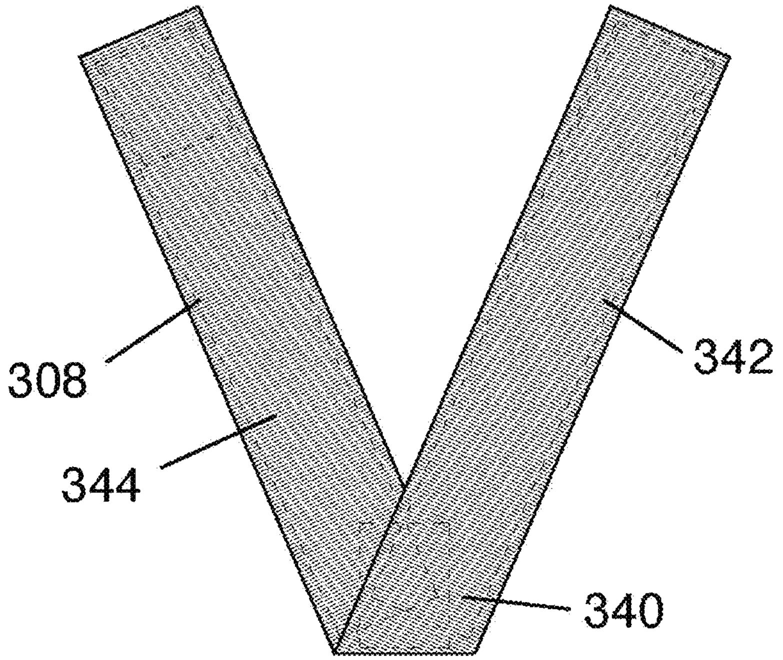
FIG. 44 illustrates an outer surface of an embodiment of a V strap.

FIG. 40 illustrates a rear view of a patient wearing an embodiment of the arm brace with a forearm of the patient in the arm sleeve member 305 coupled to the upper side surface of an arm support member 303 and a rear V strap 310 coupled to the rear portion of the arm support 303 and the rear outer surface of the wrap member 301. The rear V strap 310 can be identical to the front V strap 308. The ends of the first elongated piece 342 and the second elongated piece 344 of the rear V strap 310 are coupled to the upper and lower surfaces of the arm support member 303. The center portion 340 of the rear V strap 310 is attached to the rear surface of the waist portion 311 of the wrap member 301. The rear V strap 310 also provides support to the arm support member 303 to securely connect the arm support member 303 to the wrap member 301. FIG. 41 illustrates the fastening belt 337 is placed over the center portion 340 of the rear V strap 310. The tension of the fastening belt 337 helps to secure the center portion 340 of the rear V strap 310 to the wrap member 301.

FIG. 41 illustrates a front view of a patient wearing an embodiment of the arm brace with a forearm of the patient in the arm sleeve member 305 coupled to an upper side surface of an arm support member 303. The front V strap 308 is coupled to the arm support 303 and the front surface of the wrap member 301. The fastening belt 337 extends over the center portions 340 of the front V strap 308 and the rear V strap 310. The releasable buckles 339 at the ends of the fastening belt 337 are connected and the tension of the fastening belt 337 helps to secure the center portion 340 of the rear V strap 310 to the wrap member 301. The arm brace supports an injured arm during rehabilitation and does not require a shoulder strap, a neck strap for support and any other upper body supports.

The present disclosure, in various embodiments, includes components, methods, processes, systems, and/or apparatus substantially as depicted and described herein, including various embodiments, subcombinations, and subsets thereof. Those of skill in the art will understand how to make and use the present disclosure. The present disclosure, in various embodiments, includes providing devices and processes in the absence of items not depicted and/or described herein or in various embodiments hereof, including in the absence of such items as may have been used in previous devices or processes, e.g., for improving performance, achieving ease, and/or reducing cost of implementation. Rather, as the following claims reflect, inventive aspects lie in less than all features of any single foregoing disclosed embodiment.

What is claimed is:

1. An arm brace comprising:

a wrap member having a waist wrap portion adapted to wrap around a waist of a user;

an arm support member detachably coupled to an outer surface of the waist wrap portion of the wrap member; and a front V strap having a first elongated portion extending from a center portion to a first end, and a second elongated portion extending from the center portion to a second end, the center portion coupled to the waist wrap portion of the wrap member, the first end coupled to an upper surface of the arm support member, and the second end coupled to a lower surface of the arm support member.

2. The arm brace of claim 1 further comprising:

an arm sleeve member adapted to surround a forearm of the user, wherein a bottom surface of the arm sleeve member is supported by the upper surface of the arm support member.

3. The arm brace of claim 1 further comprising:

an arm sleeve member adapted to surround a forearm of the user, wherein an inner surface of the arm sleeve member is supported by a vertical outer surface of the arm support member.

4. The arm brace of claim 1 further comprising:

a rear V strap having a first elongated portion extending from a center portion to a first end, and a second elongated portion extending from the center portion of the rear V strap to a second end, the center portion of the rear V strap coupled to the waist wrap portion of the wrap member and the second end of the rear V strap coupled to the lower surface of the arm support member.

5. The arm brace of claim 1 further comprising:

a fastening belt attached to the outer surface of the waist wrap portion of the wrap member and an outer surface of the arm support member.

6. The arm brace of claim 1 further comprising:

a fastening belt attached to the outer surface of the waist wrap portion of the wrap member and an outer surface of the arm support member and the center portion of the front V strap is between the fastening belt and the waist wrap portion of the wrap member.

7. The arm brace of claim 1 wherein the front V strap has releasable fasteners at the center portion, the first end, and the second end and portions of the front V strap between the center portion and the first end and between the center portion and the second end do not have fasteners.

8. The arm brace of claim 1 wherein the front V strap is made of a single elongated piece of inelastic fabric that is folded at the center portion.

9. The arm brace of claim 1 wherein the portions of the front V strap between the center portion and the first end and between the center portion and the second end form an angle between 20 and 80 degrees.

10. The arm brace of claim 1 wherein the arm support member is not coupled to a neck strap or a shoulder strap.

11. An arm brace comprising:

a wrap member having a waist wrap portion adapted to wrap around a waist of a user;

an arm support member detachably coupled to an outer surface of the waist wrap portion of the wrap member;

a front V strap having a first elongated portion extending from a center portion to a first end, and a second elongated portion extending from the center portion to a second end, the center portion coupled to the waist wrap portion of the wrap member, the first end coupled to an upper surface of the arm support member, and the second end coupled to a lower surface of the arm support member; and an arm sleeve member adapted to surround a forearm of the user, wherein a bottom surface of the arm sleeve member is supported by the upper surface of the arm support member or an inner surface of the arm sleeve member is supported by a vertical outer surface of the arm support member.

12. The arm brace of claim 11 further comprising:

a rear V strap having a first elongated portion extending from a center portion to a first end, and a second elongated portion extending from the center portion of the rear V strap to a second end, the center portion of the rear V strap coupled to the waist wrap portion of the wrap member and the second end of the rear V strap coupled to the lower surface of the arm support member.

13. The arm brace of claim 11 further comprising:

a fastening belt attached to the outer surface of the waist wrap portion of the wrap member and an outer surface of the arm support member.

14. The arm brace of claim 11 further comprising:

a fastening belt attached to the outer surface of the waist wrap portion of the wrap member and an outer surface of the arm support member and the center portion of the front V strap is between the fastening belt and the waist wrap portion of the wrap member.

15. The arm brace of claim 11 wherein the front V strap has releasable fasteners at the center portion, the first end, and the second end and portions of the front V strap between the center portion and the first end and between the center portion and the second end do not have fasteners.

16. The arm brace of claim 11 wherein the front V strap is made of a single elongated piece of inelastic fabric that is folded at the center portion.

17. The arm brace of claim 11 wherein the portions of the front V strap between the center portion and the first end and between the center portion and the second end form an angle between 20 and 80 degrees.

18. The arm brace of claim 11 wherein the arm support member is not coupled to a neck strap or a shoulder strap.

* * * * *